United States Patent
Magaletta et al.

(10) Patent No.: US 9,109,247 B2
(45) Date of Patent: Aug. 18, 2015

(54) IN VITRO METHOD FOR THE DETERMINATION OF GLYCEMIC INDEX OF FOOD PRODUCTS

(75) Inventors: Robert L. Magaletta, Branchburg, NJ (US); Suzanne N. DiCataldo, Florham Park, NJ (US)

(73) Assignee: Intercontinental Great Brands LLC, East Hanover, NJ (US)

( * ) Notice: Subject to any disclaimer, the term of this patent is extended or adjusted under 35 U.S.C. 154(b) by 730 days.

(21) Appl. No.: 12/144,056

(22) Filed: Jun. 23, 2008

(65) Prior Publication Data
US 2009/0004642 A1      Jan. 1, 2009

Related U.S. Application Data

(60) Provisional application No. 61/007,534, filed on Jun. 28, 2007.

(51) Int. Cl.
C12Q 1/25    (2006.01)
C12Q 1/40    (2006.01)
C12Q 1/54    (2006.01)

(52) U.S. Cl.
CPC ... *C12Q 1/40* (2013.01); *C12Q 1/54* (2013.01)

(58) Field of Classification Search
USPC .......................................................... 435/14
See application file for complete search history.

(56) References Cited

U.S. PATENT DOCUMENTS 6,549,861 B1 *   4/2003   Mark et al. ........................ 702/76
2003/0087018 A1 *   5/2003   Arndt et al. .................... 426/618
2003/0219520 A1 *   11/2003   Shi et al. ........................ 426/549

FOREIGN PATENT DOCUMENTS

CN    1810161 A    8/2006

OTHER PUBLICATIONS

Bruggink et al., "Analysis of Carbohydrates by Anion Exchange Chromatography and Mass Spectrometry," Journal of Chromatography A, vol. 1085 pp. 104-109 (2005).*
Gouveia et al., "Homogenization of Breakfast Cereals using Cryogenic Grinding," Journal of Food Engineering, vol. 51, pp. 59-63 (2002).*
Englyst et al., Am. J. Clin. Nutr., vol. 69, pp. 448-454 (1999); of record.*
Bruggink et al., Journal of Chromatography A, vol. 1085 pp. 104-109 (2005); of record.*
Gouveia et al., Journal of Food Engineering, vol. 51, pp. 59-63 (2002) of record.*
H.N. Englyst et al., "Classification and Measurement of Nutritionally Important Starch Fractions", European Journal of Clinical Nutrition, (1992) vol. 46 (Suppl. 2), pp. S33-S50.
Hans N. Englyst et al., "Measurement of Rapidly Available Glucose (RAG) in Plant Foods: A Potential in vitro Predictor of the Glycaemic Response", British Journal of Nutrition, (1996) vol. 75, pp. 327-337.

(Continued)

*Primary Examiner* — Cherie M Stanfield
*Assistant Examiner* — Paul D. Pyla
(74) *Attorney, Agent, or Firm* — Fitch, Even, Tabin & Flannery LLP

(57) ABSTRACT

The present invention provides an in vitro method for determining the glycemic index values for various food products. The present invention provides an accurate and inexpensive in vitro method for determining the glycemic index of a wide variety of both food ingredients and finished food products.

21 Claims, 6 Drawing Sheets

(56) References Cited

OTHER PUBLICATIONS

Klaus N. Englyst et al., "Glycaemic Index of Cereal Products Explained by Their Content of Rapidly and Slowly Available Glucose", British Journal of Nutrition, (2003) vol. 89, pp. 329-339.

Y. Granfeldt et al., "An in vitro Procedure Based on Chewing to Predict Metabolic Response to Starch in Cereal and Legume Products", European Journal of Clinical Nutrition, (1992) vol. 46, pp. 649-660.

Klaus Englyst et al., "Rapidly Available Glucose in Foods: An In Vitro Measurement That Reflects the Glycemic Response", American Journal of Clinical Nutrition, Bethesda, MD, U.S., vol. 69, No. 3, Mar. 1, 1999, pp. 448-454.

Anne Flint et al., "The Use of Glycaemic Index Tables to Predict Glycaemic Index of Composite Breakfast Meals" British Journal of Nutrition, vol. 91, No. 6, Jun. 2004, pp. 979-989.

David Trout et al., "Prediction of Glycemic Index Among High-Sugar, Low-Starch Foods", International Journal of Food Sciences and Nutrition, vol. 50, No. 2, Mar. 1999, pp. 135-144.

Magaletta, Robert L. et al., In Vitro Method for Predicting Glycemic Index of Foods Using Simulated Digestion and an Artificial Neural Network, Cereal Chemistry, vol. 87, No. 4, Jul.-Aug. 2010, pp. 363-369.

Alfenas, Rita C. G. and Mattes, Richard D., Influence of Glycemic Index/Load on Glycemic Response, Appetite, and Food Intake in Healthy Humans, Diabetes Care, vol. 28, 2005, pp. 2123-2129, [online], [retrieved on Aug. 8, 2009]. Retrieved from the Internet: <URL: http://care.diabetesjournals.org/cgi/content/full/28/9/2123>, 12 pages.

Anderson, James W. et al., Carbohydrate and Fiber Recommendations for Individuals with Diabetes: A Quantitative Assessment and Meta-Analysis of the Evidence, Journal of the American College of Nutrition, vol. 23, No. 1, 2004, pp. 5-17.

Araya, H. et al., A comparison between an in vitro method to determine carbohydrate digestion rate and the glycemic response in young men, European Journal of Clinical Nutrition, vol. 56, 2002, pp. 735-739.

Atkinson, Fiona S. et al., International Tables of Glycemic Index and Glycemic Load Values: 2008, Diabetes Care, vol. 31, No. 12, Dec. 2008, pp. 2281-2283.

Brand, Janette C. et al., Low-Glycemic Index Foods Improve Long-Term Glycemic Control in NIDDM, Diabetes Care, vol. 14, No. 2, Feb. 1991, pp. 95-101.

Cheng, Guo et al., Relation of Dietary Glycemic Index, Glycemic Load, and Fiber and Whole-Grain Intakes During Puberty to the Concurrent Development of Percent Body Fat and Body Mass Index, American Journal of Epidemiology, vol. 169, No. 6, 2009, pp. 667-677.

Das, Sai Krupa et al., Long-term effects of 2 energy-restricted diets differing in glycemic load on dietary adherence, body composition, and metabolism in CALERIE: a 1-y randomized controlled trial, American Journal of Clinical Nutrition, vol. 85, No. 4, Apr. 2007, pp. 1023-1030, [online], [retrieved on Apr. 8, 2009], Retrieved from the Internet: <http://www.ajcn.org/cgi/content/full/85/4/1023, 17 pages.

DeVries, Jonathan W., Physiological Effects, Measure Effect of Carbohydrates rather than Amount, Presentation from Dietary Fiber Methods AOAC Workshop, AOAC International, Gaithersburg, Maryland, 18 pages.

Fao/Who, Carbohydrates in Human Nutrition, FAO Food and Nutrition Paper 66, Reprinted 1998, Rome, Apr. 14-18, 1997, [online], [retrieved on Apr. 21, 2014]. Retrieved from the Internet: <URL: http://www.fao.org/docrep/w8079e/w8079e00.htm#Contents>, 161 pages.

Foster-Powell, Kaye et al., International table of glycemic index and glycemic load values: 2002, American Journal of Clinical Nutrition, vol. 76, 2002, pp. 5-56.

Frost, G. et al., Insulin Sensitivity in Women at Risk of Coronary Heart Disease and the Effect of a Low Glycemic Diet, Metabolism, vol. 47, No. 10, Oct. 1998, pp. 1245-1251.

Gannon, Mary C. et al., The Insulin and Glucose Responses to Meals of Glucose Plus Various Proteins in Type II Diabetic Subjects, Metabolism, vol. 37, No. 11, Nov. 1988, pp. 1081-1088.

Garsetti, Marcella et al., The Glycemic and Insulinemic Index of Plain Sweet Biscuits: Relationships to in Vitro Starch Digestibility, Journal of the American College of Nutrition, vol. 24, No. 6, 2005, pp. 441-447.

Halton, Thomas L. et al., Low-Carbohydrate-Diet Score and the Risk of Coronary Heart Disease in Women, The New England Journal of Medicine, vol. 355, No. 19, Nov. 2006, pp. 1991-2002.

Hare-Bruun, Helle et al., Should glycemic index and glycemic load be considered in dietary recommendations?, Nutrition Reviews, vol. 66, No. 10, 2008, pp. 569-590.

Henry, C. Jeya K. et al., The influence of adding fats of varying saturation on the glycaemic response of white bread, International Journal of Food Sciences and Nutrition, vol. 59, No. 1, Feb. 2008, pp. 61-69.

Jenkins, David J. A. et al., Glycemic index of foods: a physiological basis for carbohydrate exchange, American Journal of Clinical Nutrition, vol. 34, Mar. 1981, pp. 362-366.

Jenkins, Alexandra L. et al., Comparable Postprandial Glucose Reductions with Viscous Fiber Blend Enriched Biscuits in Healthy Subjects and Patients with Diabetes Mellitus: Acute Randomized Controlled Clinical Trial, Croatian Medical Journal, vol. 49, No. 6, Dec. 2008, pp. 772-782, [online], [retrieved on Apr. 8, 2009]. Retrieved from the Internet: <URL: http://www.pubmedcentral.nih.gov/articlerender.fcgi?artid=2621039>, 19 pages.

Jentjens, R. L. P. G. and Jeukendrup, A. E., Effects of pre-exercise ingestion of trehalose, galactose and glucose on subsequent metabolism and cycling performance, European Journal of Applied Physiology, vol. 88, 2003, pp. 459-465.

Livesey, Geoffrey, Health potential of polyols as sugar replacers, with emphasis on low glycaemic properties, Nutrition Research Reviews, vol. 16, 2003, pp. 163-191.

Moghaddam, Elham et al., The Effects of Fat and Protein on Glycemic Responses in Nondiabetic Humans Vary with Waist Circumference, Fasting Plasma Insulin, and Dietary Fiber Intake, Journal of Nutrition, vol. 136, Oct. 2006, pp. 2506-2511, [online], [retrieved on Apr. 8, 2009]. Retrieved from the Internet: <URL: http://jn.nutrition.org/cgi/content/full/136/10/2506>, 13 pages.

Osborne, Jason W., Prediction in Multiple Regression, Practical Assessment, Research & Evaluation, vol. 7, No. 2, 2000, pp. 1-4, [online], [retrieved on Apr. 11, 2014]. Retrieved from the Internet: <URL: http://ericae.net/pare/78~getvn.html>, 8 pages.

Pi-Sunyer, F. Xavier, Glycemic index and disease, American Journal of Clinical Nutrition, vol. 76 (suppl), 2002, pp. 290S-298S.

Wolever, Thomas M. S. et al., The glycemic index: methodology and clinical implications, American Journal of Clinical Nutrition, vol. 54, 1991, pp. 846-854.

Wolever, Thomas M. S. et al., Beneficial Effect of Low-Glycemic Index Diet in Overweight NIDDM Subjects, Diabetes Care, vol. 15, No. 4, Apr. 1992, pp. 562-564.

WHO/FAO, Diet Nutrition and the Prevention of Chronic Diseases, WHO Technical Report Series 916, World Health Organization, Geneva, Switzerland, 2003, Geneva Jan. 28-Feb. 1, 2002, 160 pages.

* cited by examiner

IN VITRO METHOD FOR THE DETERMINATION OF GLYCEMIC INDEX OF FOOD PRODUCTS

RELATED APPLICATIONS

This application claims benefit of U.S. Provisional Application Ser. No. 61/007,534 with an effective date of Jun. 28, 2007, which is hereby incorporated by reference.

FIELD OF THE INVENTION

The present invention relates to an in vitro method for determining the glycemic index (GI) values for various food products. The present invention provides an accurate and inexpensive in vitro method for determining the glycemic index of a wide variety of both food ingredients and finished food products.

BACKGROUND OF THE INVENTION

Interest in the glycemic index of food products has significantly increased in recent years. The glycemic index is an indicator of the relative glycemic response to dietary carbohydrates in a given food product upon human digestion and allows foods to be ranked based on the rate of release and absorption of carbohydrates. In effect, the glycemic index allows identification of so-called "good carbs" (i.e., carbohydrates with relatively low glycemic indexes) and so-called "bad carbs" (i.e., carbohydrates with relatively high glycemic indexes). Carbohydrate-conscious consumers and health care providers can use the glycemic index or related values to assist in food selections.

The glycemic index ranks carbohydrates on a scale of 0 to 100 based on changes in blood sugar levels after eating. Foods with a high GI are thought to be rapidly digested and absorbed, thereby leading to marked fluctuations in blood sugar levels. Low glycemic index values are though to produce more gradual rises, and thus flattened fluctuations, in blood sugar and insulin levels due to their slower digestion and absorption by the body. Generally, low glycemic index foods are defined as having a glycemic index of 55 or less, medium glycemic index foods as having a glycemic index of 56 to 69, and high glycemic index foods as having a glycemic index of 70 or higher.

The consumption of high-glycemic index foods generally appears to result in higher and more rapid increases in blood glucose levels than the consumption of low-glycemic index foods. Rapid increases in blood glucose signal the pancreas to increase insulin secretion. High insulin levels induced by consumption of high-glycemic index foods may cause a sharp decrease in blood glucose levels (hypoglycemia) whereas consumption of low-glycemic index foods are generally thought to result in lower and more sustained increases in blood glucose and lower insulin demands. Low glycemic diets have been reported to improve both glucose and lipid levels in people with diabetes (type 1 and type 2). Low glycemic diets have also been reported to result in benefits in weight control because they help control appetite and delay hunger. Low GI diets may also reduce insulin levels and insulin resistance. Recent studies from Harvard School of Public Health report that the risks of diseases such as type 2 diabetes and coronary heart disease are strongly influenced by the glycemic index of the overall diet. The World Health Organization (WHO) and Food and Agriculture Organization of the United Nations have recommended that people in industrialized countries base their diets on low glycemic index foods in order to prevent the most common diseases of affluence, such as coronary heart disease, diabetes, and obesity. Thus, it is often recommended that consumers modify their overall diets such that the relative amount of low glycemic index foods is increased at the expense of high glycemic index foods. Glycemic index values can be used to assist consumers and health care providers in selecting foods and possibly reducing the risk of certain diseases.

The glycemic index of a given food product is usually determined in vivo by monitoring the blood glucose level of a group of human subjects (usually about 6 or more individuals) who have ingested the food product; the blood glucose response for the food product is compared to that stimulated by ingestion of a control substance of known glycemic index over a fixed period of time and the glycemic index is calculated. The in vivo glycemic index determination method is generally considered the "gold standard" in this area. In the currently accepted test protocol, measured portions of a test food containing 10 to 50 grams of carbohydrate are fed to 6 or more healthy people after an overnight fast. Blood samples, usually from finger-pricks, are taken before the food consumption (time zero) and at 15-30 minute intervals in the two hours immediately after the food consumption and analyzed for blood glucose levels. The resulting data (typically about 7 data points) are used to prepare a blood sugar response curve (i.e., blood glucose level plotted against time) for the two hour period after consumption of the test food. The area under the blood sugar curve is related to the total rise in blood glucose levels after eating the test food. A similar test is carried out, again with overnight fasting, with the same individuals consuming an equal-carbohydrate portion of glucose sugar (the reference food having, by definition, a glycemic index of 100) or white bread having a defined GI value; the two-hour blood glucose response curves are determined and the area under the curves is measured in the same manner as done for the test food. The glycemic index of the test food is calculated by dividing the area under the curve for the test food by the area under the curve for the reference food and multiplying by 100. The use of a standard food is important for reducing the confounding influence of differences in the physical and/or other characteristics of the subjects as well as to match the physical form of the test samples (i.e., standard aqueous glucose solution for beverage determinations and standard white bread for solid food determinations). Since only about 7 data points (over a two hour period) are used to generate the blood sugar curve and the curve is assumed to pass smoothly through these limited data points, errors could arise if the glucose generation is significantly increased or decreased between the actual data points taken.

The average of the glycemic indexes from all test subjects is taken as the glycemic index of the food. Of course, the accuracy of the determination depends, at least in part, on compliance of the test subjects regarding the test protocols and the validity of the assumption that the physical and/or other characteristics of the individual subjects remains essentially constant for both the test and reference food determinations.

Since such in vivo glycemic index determination methods generally require human subjects as well as being costly and time consuming, there has been considerable interest in developing in vitro test protocols. One in vitro method, based on studies by K. N. Englyst and co-workers and illustrated in FIG. 1, involved the measurement of glucose released from a test food during timed incubation at 37° C. with a mixture of digestive enzymes using a calorimetric endpoint to determine the glucose level. Englyst et al., Brit. J. Nutr., 75, 327-337 (1996). This in vitro method has more recently been modified to include a HPLC endpoint to determine the amount of glucose released. Englyst et al., Am. J. Clin. Nutr., 69, 448-454 (1999) (hereinafter referred to as the "Englyst method" or the "in vitro Englyst method").

The Englyst method involves mincing (or otherwise crushing or breaking up) a known amount of a test food (generally to contain about 0.5 g carbohydrate). The minced samples are incubated at 37° C. for 30 minutes with mixing in 10 ml 0.05 M HCl containing pepsin (5 g/l; to effect hydrolysis of protein) and guar gum (5 g/l; to help maintain food particles in suspension throughout the analysis). After this initial incubation, the samples are buffered to pH 5.2 using 0.5 M sodium acetate. An enzyme mixture (containing specific amounts of pancreatin, amyloglucosidase, and invertase) is then added to the buffered sample and the sample placed in a shaking water bath at 37° C. (time=0). Small glass balls are included in the samples to mechanically disrupt the physical structure of the samples during the main incubation; the added guar gum helps keep the sample in suspension by stabilizing the viscosity of the samples. At exactly 20 minutes into the main incubation, an aliquot of the sample is removed and added to absolute ethanol with mixing to stop the hydrolysis; this sample is used to determine $G_{20}$ (i.e., the glucose released after 20 minutes; also referred to as "rapidly available glucose" or RAG) using HPLC. The remainder of the sample is maintained in the 37° C. bath for an additional 100 minutes at which time a second aliquot of the sample is removed and added to absolute ethanol with mixing to stop the hydrolysis; this sample is used to determine $G_{120}$ (i.e., the glucose released after 120 minutes) using HPLC. The remainder of the sample is then treated as illustrated in FIG. 1 by the addition of additional enzymes and then exposure to temperatures up to 100° C. to force complete hydrolysis and, thus, determine the total glucose in the sample.

Comparing foods for which the glycemic index has been measured using the in vivo test method, the $G_{20}$ or rapidly available glucose values determined using the Englyst method can be correlated with the in vivo glycemic index values of known foods. Using such correlation coefficients, the Englyst method can be used to estimate glycemic index values for test foods.

The in vitro Englyst method has, however, met with considerable criticism, especially from proponents of the in vivo glycemic index method. For example, Garsetti et al., J. Am. Coll. Nutr., 24, 441-447 (2005), used the Englyst method to estimate glycemic index values (i.e., rapidly available glucose values) and then compared them with in vivo determined values for food products (i.e., cookies) having glycemic indexes in the range of about 35 to 60. As shown in FIG. 2 of Garsetti et al. (and incorporated by reference herein), a scatter plot of in vivo determined glycemic index values versus rapidly available glucose values (i.e., as determined by the Englyst method) yielded a scatter plot with an $R^2$ value of 0.25, indicating that the in vitro method had little predictive value.

Brand-Miller et al., Eur. J. Clin. Nutr., 58, 700-701 (2004), determined the in vivo glycemic index values for commercially available foods (one breakfast cereal and two snack bars) reportedly having low glycemic index values (i.e., ≤55) as determined by the Englyst in vitro test method. According to Brand-Miller et al., the three food products had mean in vivo glycemic index values (±sem) of 75±3, 68±5, and 65±5, respectively, and thus could not be classified as low glycemic index food products. These authors concluded that assumptions that the "laborious task of in vivo testing is no longer necessary for measuring the GI values for food" are simply incorrect and "strongly advise against the use of any in vitro method for producing GI values for food labeling purposes." Finally, the authors "urge food manufactures to undertake GI testing only with experienced laboratories using the standardized in vivo method."

Clearly there remains a need in the art for an accurate, precise, and reproducible in vitro method for determining the glycemic index values of food products. Moreover, there remains a need for such a method which can be applied to a large variety of food products, including solid and liquid food products. The present invention provides such in vitro testing methods.

SUMMARY OF THE INVENTION

The present invention provides an in vitro analytical method which allows the improved prediction of the glycemic index of a food product from the levels of protein, fat, and sugars/sugar alcohols generated using a simulated digestion of the food product with enzymes. Current glycemic index determination methods generally require human subjects and are both costly and time consuming. The inventive method is capable of determining the glycemic index of up to about 15 food samples in one day by one analyst at significantly reduced costs relative to the traditional method using human subjects. Glycemic index values determined using the present inventive method show very high correlation with results obtained using the traditional test using human subjects. Moreover, this present inventive method can be used with a wide variety of food products, including solid food products as well as semi-solid food products (e.g., yogurt and the like) and liquid food products (e.g., beverages and the like).

The present invention provides an in vitro method for determining glycemic index for a test food product, said method comprising (1) determining protein content and fat content of the test food product;

(2) providing the test food product in an essentially homogeneous and finely divided state to provide a test food sample;

(3) digesting an amount of the test food sample in the essentially homogeneous and finely divided state sufficient to provide a standardized amount of available carbohydrate with a mixture of digestive enzymes for a fixed period of time to provide a digested sample;

(4) treating the digested sample in its entirety immediately upon the fixed period of time to stop enzymatic reactions;

(5) determining amounts of glucose and at least two sugars or sugar alcohols selected from the group of fructose, galactose, lactose, sucrose, and maltitol in the digestive sample from step (4); and (6) calculating the glycemic index of the test food product from data obtained in steps (1) and (5) for the test food product using a predictive equation or a predictive technique derived from multivariate analysis of calibration data for calibration samples wherein the calibration data is of same type and obtained in same manner as the data for the test food product determined in steps (1) and (5) and wherein the calibration samples have known in vivo glycemic index values.

The present invention also provides an in vitro method for determining glycemic index for a test food product, said method comprising (1) determining protein content and fat content of the test food product;

(2) providing the test food product in an essentially homogeneous and finely divided state to provide a test food sample wherein the test food product is ground at essentially liquid nitrogen temperatures;

(3) digesting an amount of the test food sample in the essentially homogeneous and finely divided state sufficient to provide a standardized amount of available carbohydrate with a mixture of digestive enzymes for a fixed period of time to provide a digested sample;

(4) treating the digested sample in its entirety immediately upon the fixed period of time to stop enzymatic reactions;

(5) determining amounts of glucose and at least two sugars or sugar alcohols selected from the group of fructose, galactose, lactose, sucrose, and maltitol in the digestive sample from step (4); and (6) calculating the glycemic index of the test food product from data obtained in steps (1) and (5) for the test food product using a predictive equation or a predictive technique derived from multivariate analysis of calibration data for calibration samples wherein the calibration data is of same type and obtained in same manner as the data for the test food product determined in steps (1) and (5) and wherein the calibration samples have known in vivo glycemic index values.

The present in vitro method can be used to determine glycemic index values of solid, semi-solid, and liquid food products with significantly improved accuracy and precision as compared to currently available in vitro methods. Indeed, the accuracy and precision obtainable by the current inventive method is comparable to commercially available in vivo methods but with significant savings in both time and costs.

For purposes of this invention, "essentially homogeneous and finely divided state" is intended to mean a degree of grinding equivalent to grinding the food item at temperatures sufficiently low such that the food item is a brittle solid. Generally, temperatures lower than about −40° C., temperatures preferably below about −78° C., and more preferably temperatures at about temperatures obtainable using liquid nitrogen (−196° C.) are sufficient for grinding most food items which are solid or semi-solid at ambient temperatures. It is also generally preferred that ambient temperature solid materials are broken up or coarsely ground before such low temperature grinding. In one preferred embodiment, and especially for solid or semi-solid materials at ambient temperatures, grinding is accomplished using a liquid nitrogen-cooled grinding mill at or close to liquid nitrogen temperature. In many cases, liquid food products will not require any grinding since they are essentially homogeneous and the components are soluble in the carrier; if desired, however, such liquid food products may be also be ground at lower temperatures. Semi-solid materials may or may not require such low temperature grinding to obtain an essentially homogeneous and finely divided state. Thus, for example, a plain yogurt need not be further ground whereas a yogurt with fruit or other solid ingredients therein preferably is ground at low temperatures to obtain an essentially homogeneous and finely divided state. Further guidance on the required "homogeneous and finely divided state" can be found in the examples included with this specification.

Preferably the amounts of glucose and at least two sugars or sugar alcohols selected from the group of fructose, galactose, lactose, sucrose, and maltitol in the digestive sample from step (4) are determined using high performance liquid chromatography (HPLC) or equivalent quantitative methods. Preferably high performance ion chromatography (HPIC) is used to determine the amounts of sugars released during the treatment with enzymes. More preferably, the amounts of glucose, fructose, galactose, lactose, sucrose, and maltitol in the digestive sample from step (4) are determined using high performance ion chromatography (HPIC).

BRIEF DESCRIPTION OF THE FIGURES

FIG. 4B plots in vivo GI versus RAG/(% available carbohydrate); FIG. 4C plots in vivo GI versus RAG. Using the Englyst calculation techniques on data set of Example 2 yielded $R^2$ values of 0.41 and 0.68 for the scatter plots shown in FIGS. 4B and 4C, respectively.

FIG. 5B plots in vivo GI versus RAG/(% available carbohydrate); FIG. 5C plots in vivo GI versus RAG. Using the Englyst calculation techniques on data set of Example 3 yielded $R^2$ values of 0.56 and 0.58, respectively, for the scatter plots shown in FIGS. 5B and 5C, respectively.

DETAILED DESCRIPTION OF THE INVENTION

Figure 1:
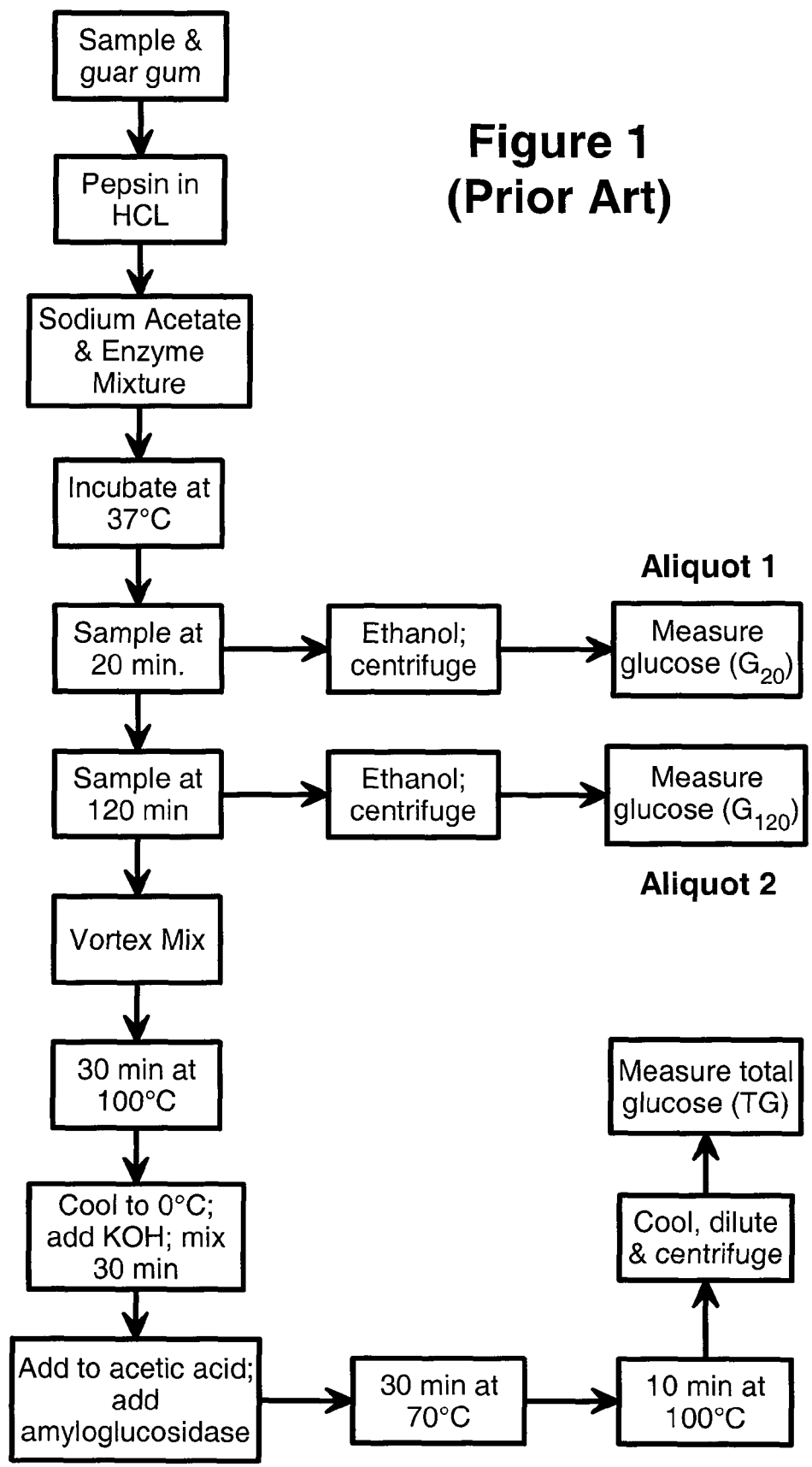
FIG. 1 provides a flow chart describing an in vitro prior art method (i.e., the Englyst method) for estimating glycemic index and related values.

The present invention provides an in vitro analytical method which allows the improved prediction of the glycemic index of a food product from the levels of protein, fat, and sugars/sugar alcohols liberated using a simulated digestion of the food product with enzymes. Current glycemic index determination methods generally require human subjects and are both costly and time consuming. The inventive method is capable of determining the glycemic index of up to about 15 food samples in one day by one analyst at significantly reduced costs relative to the traditional method using human subjects. Moreover, the administrative burden of screening human subjects, obtaining informed consent, and the like is avoided in the present invention. Glycemic index values determined using the present inventive method show very high correlation with results obtained using the traditional test with human subjects. Indeed, the in vitro method may yield results that are more precise than the results from the clinical in vivo method. Since the number of calibration samples used for the in vitro method is greater (and can continue to increase as additional calibration samples (i.e., samples for which the with known in vivo GI values) are incorporated therein) than that used for a single determination using the in vivo method, the in vivo data used to calibrate the in vitro method, from which the in vitro GI results are derived, are based on the blood glucose level results of a far larger number of human subjects than that used in any single in vivo test. Moreover, this present inventive method can be used with a wide variety of food products, including solid food products as well as semi-solid food products (i.e., yogurt and the like) and liquid food products (i.e., beverages and the like).

The present invention provides an in vitro method for determining glycemic index for a test food product, said method comprising (1) determining protein content and fat content of the test food product;

(2) providing the test food product in an essentially homogeneous and finely divided state to provide a test food sample;

(3) digesting an amount of the test food sample in the essentially homogeneous and finely divided state sufficient to provide a standardized amount of available carbohydrate with a mixture of digestive enzymes for a fixed period of time to provide a digested sample;

(4) treating the digested sample in its entirety immediately upon the fixed period of time to stop enzymatic reactions;

(5) determining amounts of glucose and at least two sugars or sugar alcohols selected from the group of fructose, galactose, lactose, sucrose, and maltitol in the digestive sample from step (4); and (6) calculating the glycemic index of the test food product from data obtained in steps (1) and (5) for the test food product using a predictive equation or a predictive technique derived from multivariate analysis of calibration data for calibration samples wherein the calibration data is of same type and obtained in same manner as the data for the test food product determined in steps (1) and (5) and wherein the calibration samples have known in vivo glycemic index values.

The present invention also provides an in vitro method for determining glycemic index for a test food product, said method comprising (1) determining protein content and fat content of the test food product;

(2) providing the test food product in an essentially homogeneous and finely divided state to provide a test food sample wherein the test food product is ground at essentially liquid nitrogen temperatures;

(3) digesting an amount of the test food sample in the essentially homogeneous and finely divided state sufficient to provide a standardized amount of available carbohydrate with a mixture of digestive enzymes for a fixed period of time to provide a digested sample;

(4) treating the digested sample in its entirety immediately upon the fixed period of time to stop enzymatic reactions;

(5) determining amounts of glucose and at least two sugars or sugar alcohols selected from the group of fructose, galactose, lactose, sucrose, and maltitol in the digestive sample from step (4); and (6) calculating the glycemic index of the test food product from data obtained in steps (1) and (5) for the test food product using a predictive equation or a predictive technique derived from multivariate analysis of calibration data for calibration samples wherein the calibration data is of same type and obtained in same manner as the data for the test food product determined in steps (1) and (5) and wherein the calibration samples have known in vivo glycemic index values.

The present in vitro method can be used to determine glycemic index values of solid, semi-solid, and liquid food products with significantly improved accuracy and precision as compared to currently available in vitro methods. Indeed, the accuracy and precision obtainable by the current inventive method appears to be comparable to commercially available in vivo methods but with significant savings in both time and costs.

For purposes of this invention, "essentially homogeneous and finely divided state" is intended to mean a degree of grinding equivalent to grinding the food item at temperatures sufficiently low such that the food item is a brittle solid. Generally, temperatures lower than about −40° C., temperatures preferably below about −78° C., and more preferably temperatures at about temperatures obtainable using liquid nitrogen (−196° C.) are sufficient for grinding most food items which are solid or semi-solid at ambient temperatures. It is also generally preferred that ambient temperature solid materials are broken up or coarsely ground before such low temperature grinding. In one preferred embodiment, and especially for solid or semi-solid materials at ambient temperatures, grinding is accomplished using a liquid nitrogen-cooled grinding mill at or close to liquid nitrogen temperature. In many cases, liquid food products will not require any grinding since they are essentially homogeneous and the components are soluble in the carrier; if desired, however, such liquid food products may be also be ground at lower temperatures. Semi-solid materials may or may not require such low temperature grinding to obtain an essentially homogeneous and finely divided state. Thus, for example, a plain yogurt need not be further ground whereas a yogurt with fruit or other solid ingredients therein preferably is ground at low temperatures to obtain an essentially homogeneous and finely divided state. Further guidance on the required "homogeneous and finely divided state" can be found in the examples included with this specification.

Preferably the amounts of glucose and at least two sugars or sugar alcohols selected from the group of fructose, galactose, lactose, sucrose, and maltitol in the digestive sample from step (4) are determined using high performance liquid chromatography (HPLC) or equivalent quantitative methods. Preferably high performance ion chromatography (HPIC) is used to determine the amounts of sugars and/or sugar alcohols released during the treatment with enzymes. Even more preferably, the amounts of glucose, fructose, galactose, lactose, sucrose, and maltitol in the digestive sample from step (4) are determined using high performance ion chromatography (HPIC). Of course, for particular food samples, the digestive sample may be determined to be essentially zero for one or more of these sugars or sugar alcohols (i.e., particular sugars or sugar alcohols may be absent). In that case, the term or terms associated with the particular sugars and/or sugar alcohols will be zero (or close to zero) and the contribution to the GI for those sugars and/or sugar alcohols will be minimal.

Currently maltitol appears to be the only sugar alcohol that has been shown in the scientific literature to have an appreciable effect on blood sugar concentrations at levels normally encountered in food products. Since HPIC with the appropriate column is capable of determining many more sugars and sugar alcohols (not just maltitol), more sugars and sugar alcohols may be included in the analysis and calibration step if so desired.

An amount of the test food sample in the essentially homogeneous and finely divided state sufficient to provide a standardized amount of carbohydrate is used in the digestive step with a mixture of digestive enzymes for a fixed period of time to provide a digested sample. For purposes of this invention, the amount of the essentially homogeneous and finely divided test food sample used in the digestive step should contain a "standardized amount" of available carbohydrate. This standardized amount of available carbohydrate is selected so that sufficient sugars and/or sugar alcohols are obtained in the digestion step to allow for accurate determination of the sugar and sugar alcohols; moreover, this standardized amount of available carbohydrate allows the digestive enzymes to have similar amount of substrate to act upon. In the specific protocol illustrated in Example 1, it has generally been found that a standardized amount of available carbohydrates should be in the range of about 0.2 to about 1 g, and more preferably about 0.5 g. Higher or lower amounts can be used if sufficiently accurate determinations of the sugars and sugar alcohols can be obtained. Of course, once a standardized amount has been selected, that amount preferably is used for all determinations (including those used to calibrate the method and as well as, once calibrated, unknown samples). For the purpose of this method, available carbohydrate content is defined as the total carbohydrate content minus the dietary fiber content minus the total content of sugar alcohols other than maltitol. If additional sugar alcohols other than maltitol are to be included in the analysis and calibration, then the content of those sugar alcohols in the sample will need to be included as available carbohydrates as well.

Similarly, the fixed period for the digestive step is selected to provide sufficient sugars and/or sugar alcohols to allow for accurate determination of the sugar and sugar alcohols produced therein. In the specific protocol illustrated in Example 1, it has generally been found that fixed period should be in the range of about 15 to about 25 minutes, and more preferably about 20 minutes. Shorter or longer digestive times can be used if sufficient amounts of the sugar and/or sugar alcohols are produced to allow accurate determinations of the sugars and sugar alcohols. Of course, once a fixed time has been selected, that value should be used for all determinations (including those used to calibrate the method and as well as, once calibrated, unknown samples); in other words, a standardized digestive time should be used throughout all calibration and unknown sample determinations. Generally, efforts should be made to stop the digestive step within about ±10 seconds of the selected fixed time, and even more preferably within about ±5 seconds.

Figure 2:
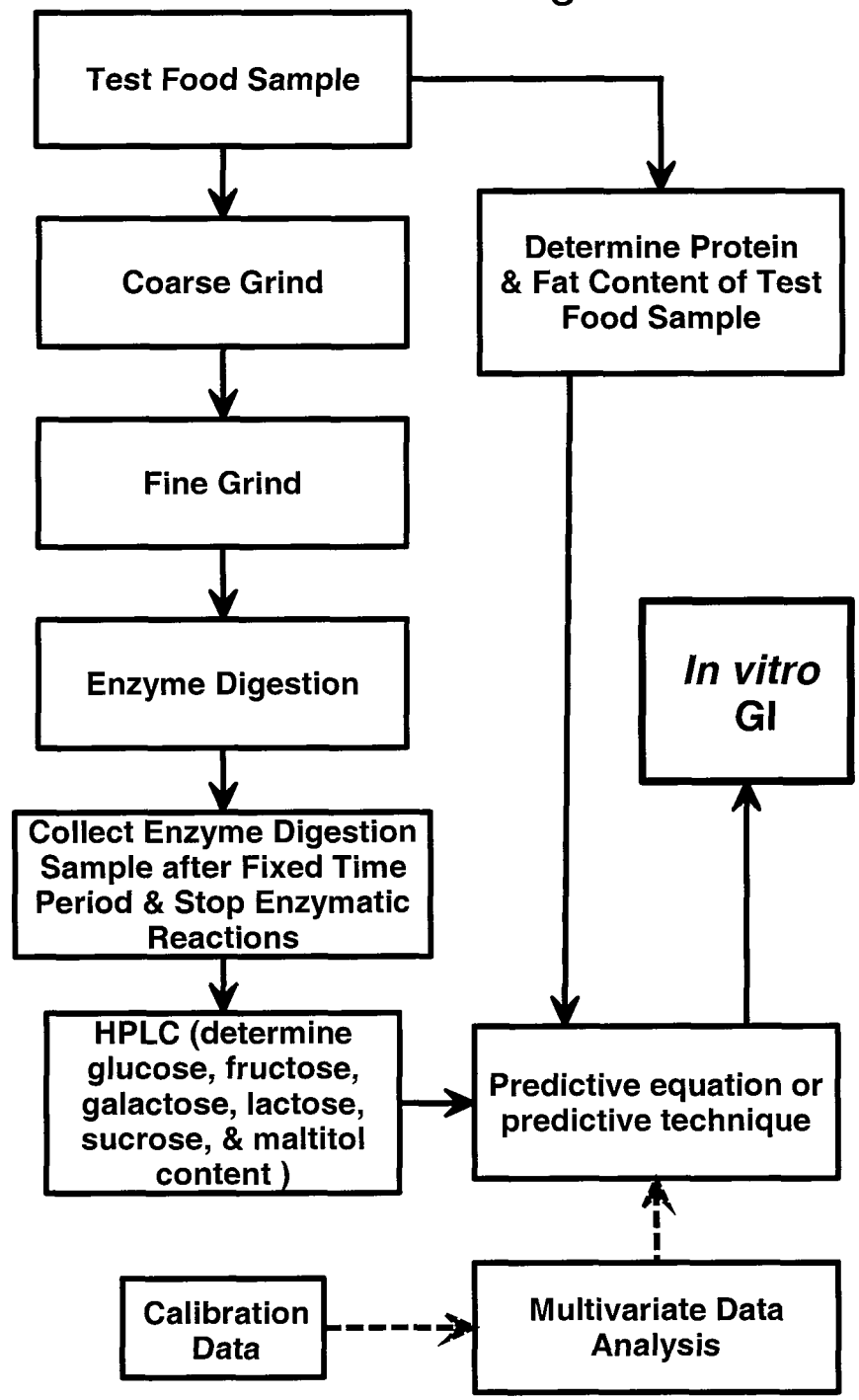
FIG. 2 provides a flow chart illustrating the in vitro method of the present invention.

FIG. 2 illustrates one embodiment of the present invention. The method begins with test food sample which may be solid, semi-solid, or liquid at ambient temperatures. As indicated above, the test food product should be rendered "essentially homogeneous and finely divided state." For most solid or semi-solid foods at ambient temperatures, this can be accomplished by grinding the food item at temperatures sufficiently low such that the food item is a brittle solid. Generally, temperatures lower than about −40° C., temperatures preferably below about −78° C., and more preferably temperatures at about temperatures obtainable using liquid nitrogen are sufficient for grinding most food items which are solid or semi-solid at ambient temperatures. It is also generally preferred that ambient temperature solid materials are broken up or coarsely ground before such low temperature grinding. Thus, as shown in FIG. 2, the test food sample is preferably coarse ground to simply break the sample in to smaller particles and then finely ground to obtain the essentially homogeneous and finely divided sample. In one preferred embodiment, and especially for solid or semi-solid materials at ambient temperatures, fine grinding is accomplished using a liquid nitrogen-cooled grinding mill at or close to liquid nitrogen temperature. In many cases, liquid food products will not require any grinding since they are essentially homogeneous and the components are soluble in the carrier; if desired, however, such liquid food products may be also be ground at lower temperatures. Semi-solid materials may or may not require such low temperature grinding to obtain an essentially homogeneous and finely divided state. Thus, for example, a plain yogurt need not be further ground whereas a yogurt with fruit or other solid ingredients therein preferably is ground at low temperatures to obtain an essentially homogeneous and finely divided state.

As one skilled in the art will understand, it is not necessary, and indeed would be difficult, to specify the resulting particle size range of the "essentially homogeneous and finely divided state." Most food samples suitable for analysis by this method will contain significant moisture levels. Thus, even when ground at liquid nitrogen temperatures (where the solids will more easily be ground because of their brittle nature at such temperature), the particles may agglomerate when allowed to return to ambient temperature because of their water contents. It is the homogeneity and finely divided state obtainable with grinding at a low temperature, at least in part, which appears to allow the accuracy and precision of the present method. Thus, in most cases, the use of low-temperature grinding is the most appropriate means of producing a homogeneous, finely-divided mixture (especially with samples having a high degree of heterogeneity such as chocolate chip cookies, trail mixes, and the like). If however, the sample contains physically-hindered starch (such as that protected from digestive enzymes by intact or partially intact cell walls), it may be more appropriate to proceed directly from a coarse grinding or crushing to the digestion, since disrupting the cell structure may result in the starch becoming too accessible to the digestive enzymes, resulting in erroneously high GI numbers. Thus, samples like potato chips are preferably not ground at low temperature. When potato chips are ground to a fine powder under low temperatures, the resulting analysis yields a GI value of about 70-75. If potato chips are only coarsely ground (which is easy to effect since potato chips are fragile at ambient temperatures), the resulting analysis yields a GI value of about 55-60, which is more in line with the values in the literature (Am. J. Clin. Nutr., 76, 5-56 (2002) reports an average value as 54±3). Thus, as those skilled in the art will appreciate, the sample preparation technique is a balance of reducing sample heterogeneity without excessively disrupting native structures that may slow starch digestion.

Once the sample is in the desired homogeneous and finely divided state, it is subject to enzymatic digestion to mimic the digestive process. Pepsin is preferably added to begin hydrolysis of proteins. Then, a mixture of enzymes is used to digest the carbohydrates present in the sample to produce sugars and solubilize the free sugars and sugar alcohols that may be present in the sample. Importantly, standardized conditions are used when determining standards (both when the model coefficients are first determined and then as a check on the overall method) and unknowns. Although these standardized conditions may vary, once they are selected they should be maintained as closely as possible throughout the calibration of the method and then in the determination of unknown samples. Generally, the mixture of enzymes contains pancreatin, amyloglucosidase (AMG), and invertase in sufficient amounts to convert essentially all of the carbohydrates into sugars and solubilize any free sugars or sugar alcohols in the sample. Incubation with the enzyme mixture is generally carried out at 37° C. for 20 minutes; once again, the exact temperature and time used for incubation (so long as they allow the enzymes to work) is less important than using the same incubation temperature and digestion time (i.e., fixed time for digestion) throughout the calibration process and unknown sample determinations.

Once the incubation has been carried out for the desired time (i.e., a standardized time of 20 minutes±10 seconds), the enzymatic reactions are immediately stopped. Preferably, ethanol is added to immediately stop the enzymatic reactions. The sample is preferably then filtered to remove any sediment or particulate matter which may be present and the sample collected. Importantly, from the time the incubation begins and until the sample is collected (i.e., after enzymatic reactions have been stopped), an integral or complete sample is maintained. That is, no separation or division of the sample are made during this time (except for the filtration after the enzymatic reactions are stopped). Maintaining the physical integrity of sample during this operation avoids errors associated with sampling what may be a non-homogeneous mixture. Thus, for example, the Englyst method may introduce significant sampling errors when an aliquot is taken from the digestion mixture after 20 minutes digestion since at that time the mixture is generally in the form of a suspension. The present method avoids such problems.

Once the final sample from the digestion mixture is obtained (preferably after filtration to remove any solid materials remaining), the sugar and sugar alcohol contents are measured using high performance liquid chromatography (HPLC) or equivalent quantitative methods. Preferably high performance ion chromatography (HPIC) is used since this technique generally gives superior separation of the sugars, especially glucose and galactose, allows the determination of both sugars and sugar alcohols (e.g., maltitol) in the same separation, and is generally less prone to interferences due to the highly selective nature of pulsed electrochemical detection. Suitable equipment and operating conditions are illustrated in Example 1. Once again, as those skilled in the art will realize, the specific equipment and operating parameters are less important than determining standardized conditions and then maintaining them throughout. Preferably the amounts of glucose and at least two sugars or sugar alcohols selected from the group of fructose, galactose, lactose, sucrose, and maltitol in the digestive sample are determined. Even more preferably, the amounts of glucose, fructose, galactose, lactose, sucrose, and maltitol in the digestive sample are determined. As noted above, additional sugars and sugar alcohols can be included in the analysis and calibration steps if desired.

Additionally the protein and fat contents for the test food sample are determined. These parameters can be determined using standard and conventional analytical techniques and/or can be calculated based on the ingredients of the test food sample. The determination of a predicted value for glycemic index is carried out using multivarient analysis such as, for example, a multiple linear regression (MLR), partial least squares (PLS), or neural net curve fitting procedures. The neural net curve fitting procedure appears to give the best fit to the data generated in the Examples and thus is generally preferred (see scatter plot in FIG. 4A). The digestion mix is analyzed via the above HPIC procedure to produce quantitative values for glucose, fructose, galactose, lactose, sucrose, and maltitol content in the final sample digest. Those values, together with the total % protein and % fat of the original sample are preferably entered to a suitable statistical software program (e.g., JMP Statistical Software), which then predicts the GI values of the original sample based on the appropriate prediction or correlation equation or predictive technique.

The prediction equation or predictive technique is derived from the data for a calibration set for which the clinical or in vivo GI values are known. This is illustrated in FIG. 2 wherein broken arrows are used to indicate the determination of the parameters for the prediction equation or predictive technique. The data is determined using the same standardized conditions and procedures as detailed above and in Example 1. The calibration set used in Example 1 includes food products and a series of pure standards for which the clinical GI values are known. The calibration standards used in Example 1 span the range of GI values from 19 to 100 and are treated in exactly the same manner as the other food samples in the calibration. All calibration samples and standards, and later all unknown samples, should be analyzed using the same standardized conditions and procedures. Using appropriate software, the data from the calibration samples and standards is used to derive an equation or other relationship which best fits the correlation between the clinical in vivo GI values and the prediction variables. Preferably, a multivariate analysis technique (e.g., MLR, PLS, or neural net) is used. Additional in vivo data from newly available calibration samples or standards can be, if desired, incorporated into the model to update and improve the prediction variables of the equation or predictive technique.

The method described herein preferably includes all the sugars listed above plus maltitol in the calibration. If, however, the samples likely to be encountered are known to not contain some of the components, they may be left out of the calibration (e.g., maltitol, galactose). Likewise, additional parameters or measurements associated with the food product (e.g., organic acid content, β-glucan content, and the like) can be included. The amount of sucrose in the digestive sample is typically found to be essentially zero since the invertase is expected to convert any sucrose present into glucose and fructose. If desired, the determination of sucrose can be used as an internal check. Thus, if the method is carried out properly the level of sucrose should be essentially zero; if significant amounts of sucrose are detected, the analysis is suspect and the sample should be repeated. Of course, this method of using sucrose as an effective internal standard should only be used if the standardized conditions and parameters selected for the method do, indeed, result in essentially no sucrose in the digestive sample. If the sample contains any substance which may inhibit invertase activity, the ability to quantitate the sucrose remaining may be useful in developing a calibration data set which takes that inhibitory effect into account in the calculation of the in vitro GI value.

The following examples are intended to illustrate the invention and not to limit it. Unless noted otherwise, all percentages and ratios are by weight. All publications cited herein are hereby incorporated by reference.

Example 1

This Example provides a detailed analytical protocol for carrying out the in vitro glycemic index determination of the present invention for both the calibration of the method and determination of unknown samples. In all cases where specific equipment, reagents, and/or specific procedures and operating parameters are suggested, it will be understood that equivalent equipment, reagents, and/or specific procedures and operating parameters can be used.

Apparatus:

1. Temperature-controlled shaking water bath (capable of about 175 strokes/min);
2. Vortex mixer;
3. Analytical balance (accurate to within ±0.0001 g);
4. Volumetric flasks, Class A, 100 ml, 1000 ml;
5. Pipets, Class A, 1 ml, 2 ml, 5 ml, 6 ml, 10 ml;
6. Glass balls, 6 mm (Fisher #11-312-D or equivalent);
7. Glass sample vials (40 ml) with screw caps (VWR #66014-389 or equivalent);
8. Plastic centrifuge tubes (50 ml) with screw caps (VWR #21008-730 or equivalent);
9. Centrifuge;
10. Spex CertiPrep 6850 freezer mill or equivalent;
11. 1 Qt. wide-mouth Mason jars;
12. Filter funnels;
13. Whatman #4 fast filter paper, 12.5 cm circles, or equivalent;
14. Ring stands;
15. Anotop 10 Plus 0.2 micron 10 mm diameter syringe filters;
16. HPIC equipment and reagents listed in section entitled "HPIC Procedure" below; and
17. JMP Statistical Software, version 5.1, SAS Institute, or equivalent.

Reagents:

1. 0.5 N Hydrochloric acid (HCl) (VWR #VW3201-1);
2. Sodium acetate (NaAc) (Acros #42425-5000);
3. Ethyl alcohol USP, 190 proof—95% (95% EtOH) (Aaper Alcohol & Chemical Co.);
4. Invertase from bakers yeast, 215 U/mg solid (Sigma #1-9274);
5. Amyloglucosidase (AMG), 300 U/ml (Novozymes #AMG 300 L) (note: should be stored at 0-25° C. and used within 3 months from date of delivery);
6. Pepsin from porcine stomach mucosa, 439 U/mg solid (Sigma #P-7000)
7. Guar gum (Sigma #G4129-250G);
8. Pancreatin from porcine pancreas (Sigma #P-7545);
9. Deionized water ($H_2O$); and
10. Liquid nitrogen; and
11. Pure standards of anhydrous glucose, fructose, sucrose, lactose, galactose, and maltitol (Minimum 99% purity, Sigma Aldrich Company or equivalent; should be stored in desiccator when not in use).

Solutions:

1. 0.05N HCl solution (dilute 100 ml 0.5N HCl to 1000 ml with deionized water);
2. Pepsin/Guar Gum Solution (2195 U/ml pepsin and 0.5% guar gum (W/V) in 0.05 N HCl)—dissolve 0.5 g pepsin and 0.5 g guar gum in 100 ml 0.05 N HCl;
3. Invertase Stock Solution (510.7 U/ml in H2O)—dissolve 100 mg invertase in 42.10 ml $H_2O$;
4. 0.5 M Sodium Acetate Solution (0.5 M NaAc in $H_2O$)—dissolve 4.10 g sodium acetate in 100 ml $H_2O$;
5. 66% Ethyl Alcohol Solution (66% EtOH) (V/V)—mix 347 ml ethyl alcohol with 153 m; deionized water in a 1 quart mason jar and cap; this is enough solution for one sample; and
6. Enzyme Solution (recipe for one sample—136 mg/ml pancreatin, 13.4 U/ml AMG and 25.43 U/ml invertase):
    I. Weigh 1.0 g pancreatin into a 50 ml centrifuge tube;
    ii. Add 6.67 ml $H_2O$ and vortex mix for 10 min to dissolve thoroughly (a stir bar or glass balls may be needed if preparing solution for use with for multiple samples);
    iii. Centrifuge at 2000 rpm for 10 min; and
    iv. For each test sample, transfer 6 ml supernatant to another 50 ml centrifuge tube, add 296 µl AMG and 330 µl Invertase Stock Solution.

Sample Preparation for Solid Sample:

1. Sample is placed in Waring Laboratory Micronizer and ground until sample is well mixed (generally 30 to 60 seconds is sufficient).
2. A 3 ounce/100 g sub-sample from the Micronizer is then cryogenically ground in the Spex CertiPrep 6850 Freezer/Mill. The Spex CertiPrep 6850 Freezer/Mill is an impact grinder cooled by liquid nitrogen. The sample, embrittled by cold, is pulverized by the hammering of the impactor against the end plugs of the vial. The sample should occupy between about one third to about one half the height of the grinding vial (#6801).
3. The 6850 Freezer/Mill can be programmed using its keyboard. Control Modes and Conditions: Cycle 1—Grinding Time 1.5 min; Rate (impact frequency) 10 cycles per second; and Pre-cooling Time 4 min. (i.e., time before grinding starts).
4. At the conclusion of the grinding cycle, empty the vial into a suitable container and cap.

Digestion Procedure:

1. Weigh an amount of sample equivalent to 0.50 g available carbohydrate (available carbohydrate=total carbohydrates minus fiber minus sugar alcohols other than maltitol) into a 40 ml glass screw cap vial, add 5 ml $H_2O$, 10 ml freshly prepared pepsin/guar gum solution and 5 glass balls. A sample blank consisting of 0.5 g of water is also run with each batch of samples.
2. Vortex mix the capped vial vigorously and place horizontally in a 37° C. shaking water bath (175 strokes/min); shake for 30 min to allow hydrolysis of proteins by pepsin.
3. Add 5.0 ml 0.5 M NaAc (equilibrated to 37° C.) to the vial.
4. Mix, then add 5 ml enyzme solution. Mix by inversion. The pH of this digestion mixture should be about 5.
5. Immediately place the original sample horizontally into the 37° C. shaking water bath to continue the enzyme reaction. Shake for 20 minutes. Remove sample vial from shaker after 20 minutes (±10 seconds).
6. Immediately pour the contents of the vial into a mason jar containing 500 ml 66% EtOH to stop the reactions. Rinse the vial with several drops of EtOH solution from mason jar, cap the mason jar, then mix once by inversion. Immediately filter a portion of the contents of the mason jar through fast filter paper into a 40 ml screw cap vial, cap, and save for HPIC analysis.

The digested sample is then analyzed for sugar and sugar alcohol content by HPIC as detailed below:

1. Equipment—Dionex Chromatography System Consisting of:

High-Performance Pump;

Liquid Chromatography Module;

Pulsed Electrochemical Detector;

Eluent Degas Module; and

Dionex Chromeleon Chromatography Workstation.

2. Reagents and Standards

Deionized water, 18 MΩ-cm resistance;

Sodium hydroxide solution, 50% w/w, low carbonate; and

Galactose, glucose, fructose, sucrose, lactose, and maltitol pure standards.

3. Conditions:

Columns: CarboPac™ PA1 analytical (4×250 mm) and AminoTrap guard (4×50 mm) columns;

Operating Conditions Pressure: 1200-1500 psi; Inj. Volume: 10 μL; Eluent: 21 mM Sodium hydroxide (may be adjusted to achieve the best separation with each column; Note: CarboPac PA1 should be washed with 200 mM NaOH between runs to prevent carbonate from building up on the column); Flow Rate: 1 mL/min; and Detection: Pulsed amperometry, disposable gold working electrode and standard carbohydrate setting.

4. Preparation of Solutions:

a) Eluent: dilute 1.6725 g of NaOH solution (50% w/w, low carbonate) in 1.0 L of deionized water (18 MΩ-cm resistance);

b) Column Washing Solution: 200 mM NaOH: dilute 16 g of NaOH solution (50% w/w, low carbonate) in 1.0 L of deionized water (18 MΩ-cm resistance);

5. Preparation of Standards:

Accurately weigh about 0.1000 gm each of above 6 standards (i.e., galactose, glucose, fructose, sucrose, lactose, and maltitol pure standards) into a 100 ml volumetric flask to make a 1000 ppm mixed standard with deionized water (18 MD-cm resistance). Dilute this solution to produce the following working standards:
 a) 1 ml diluted to 1000 ml including 66 ml ethyl alcohol (195 proof) to make 1 ppm standard;
 b) 2 ml diluted to 100 ml including 6.6 ml ethyl alcohol (195 proof) to make 20 ppm standard;
 c) 5 ml diluted to 100 ml including 6.6 ml ethyl alcohol (195 proof) to make 50 ppm standard; and
 d) 10 ml diluted to 100 ml including 6.6 ml ethyl alcohol (195 proof) to make 100 ppm standard.

6. Sample Preparation and Injection:

The final digest solution from the digestion procedure is diluted 1:10 in deionized water, then filtered through a 0.2 micron Anotop10 Plus syringe filter into an autosampler vial. A sample of the solution (10 μl) is then injected into the chromatograph.

7. Chromatography Gradient Conditions:

| | Solvent (%) | | |
|---|---|---|---|
| TIME (min) | 200 mM NaOH | 21 mM NaOH | Comments |
| −20 | 100 | 0 | Regenerate Column |
| −9 | 0 | 100 | Re-equilibrate Column |
| 0 | 0 | 100 | Sample Injection |
| 36 | 0 | 100 | Completed |

8. Electrochemical Detector Parameters: Use Preloaded Waveform with Ag/AgCl Reference Electrode:

| Time | Potential | Integration |
|---|---|---|
| 0.0 | +0.10 | |
| 0.20 | +0.10 | Begin |
| 0.40 | +0.10 | End |
| 0.41 | −2.00 | |
| 0.42 | −2.00 | |
| 0.43 | −0.60 | |
| 0.44 | −0.10 | |
| 0.55 | −0.10 | |

Column storage solution: 21 mM Sodium hydroxide (NaOH)

9. Quantitative Determination of Sugars and Maltitol:

Mixed standards of 1, 20, 50, and 100 ppm are injected into the HPIC, and a calibration curve is constructed using the appropriate software for the chromatography system. If the concentration of one or more of the analytes in the sample exceeds that of the highest standard, the calibration curve should be expanded to include standards with concentrations higher than those found in the most concentrated sample. The sample blanks or test samples are then injected into the HPIC and the concentrations of galactose, glucose, fructose, sucrose, lactose, and maltitol are calculated from the calibration curve using peak areas. Concentrations from the calibration curve are multiplied by 10 to account for the 10-fold dilution of the samples and sample blank in step 6 above, and reported in terms of % of each analyte in the final digest.

The concentration values (%) for each analyte in the sample blank should be subtracted from those of each analyte in each sample to arrive at the blank-corrected sample concentration values (%).

Figure 3:
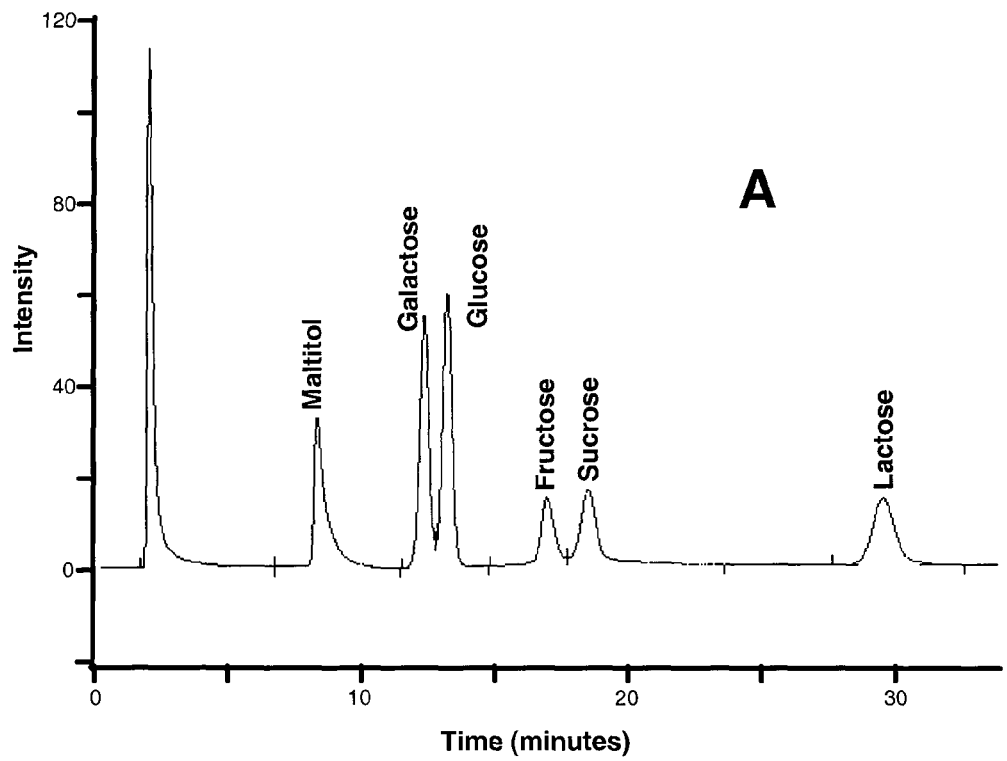
FIG. 3 provides typical chromatograms of a mixed standard (Panel A) and a typical unknown sample (Panel B) obtained in the in vitro method described in Example 1.
Figure 3:
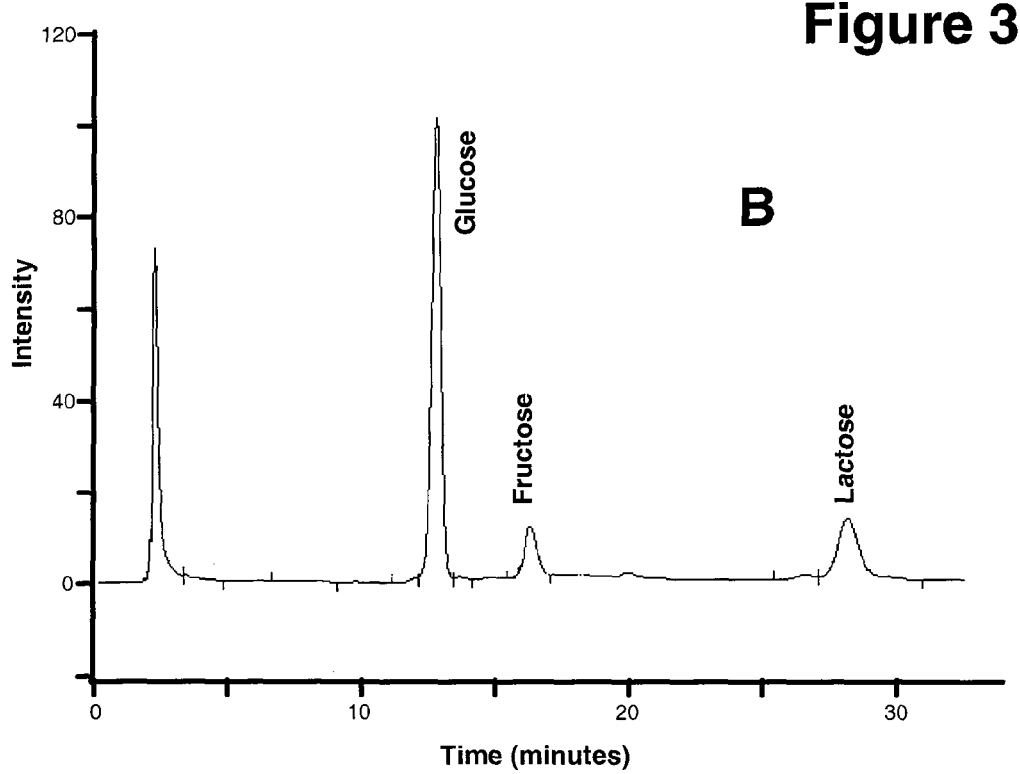

Example chromatograms of mixed standard (Panel A) and a typical unknown or test sample (Panel B) are shown in FIG. 3.

Calculations:

The determination of a predicted value for glycemic index is accomplished via a multiple linear regression (MLR), partial least squares (PLS) or neural net curve fitting procedure. The digestion mix is analyzed via the above HPIC procedure to produce blank-corrected quantitative values for glucose, fructose, galactose, lactose, sucrose, and maltitol content in the final sample digest. Those values, together with the total % protein and % fat of the original sample, determined by analysis or calculation from ingredient values, are entered into a JMP Statistical Software spreadsheet, which then predicts the GI values of the original sample based on a prediction equation or predictive technique as appropriate for the specific curve fitting procedure used.

The prediction equation predictive technique is derived from the data for a calibration set for which the clinical in vivo GI values are known. The calibration set includes food products and a series of pure standards for which the clinical GI values are known. These standards used to calibrate the method in Example 2 span the range of GI values from 19 to 100 and are treated in exactly the same manner as the other food samples in the calibration. After they are analyzed, additional samples and/or standards may be added to the calibration set and the model parameters recalculated if the in vivo GI values are known for those samples and/or standards; such additions should strengthen the calibration by making the calibration set more broadly representative of the population of food samples for which GI may be determined. Thus, the prediction equation or predictive technique can be updated to include newly available or improved in vivo data. All calibration samples and standards were previously analyzed via the procedure described above, and the JMP Statistical Software was then used to fit an equation to the data which best fits the relationships between the clinical GI values and the prediction variables, using either the MLR, PLS, or neural net methods.

The method described herein includes all the sugars plus maltitol in the calibration. If, however, the samples likely to be encountered are known to not contain some of the components, they may be left out of the calibration (e.g., maltitol, galactose). The amount of sucrose in the digested sample is typically found to be essentially zero, due to the action of invertase, which converts any sucrose present into glucose and fructose. If, however, the sample contains an invertase activity inhibitor, the ability to include sucrose levels may be useful in developing calibration equations which takes that inhibitory effect into account in the calculation of the in vitro GI value. Maltitol is the only sugar alcohol that has been shown in the scientific literature to have an appreciable effect on blood sugar concentrations at levels normally encountered in food products. Since HPIC with the appropriate column is capable of determining many more sugars and sugar alcohols (not just maltitol), more sugars and sugar alcohols may be included in the analysis and calibration step if so desired.

Unknown samples are predicted by entering the % protein in the sample, % fat in the sample, and the blank-corrected concentration values for % glucose in the digest, % fructose in the digest, % lactose in the digest, % sucrose in the digest, % galactose in the digest, and % maltitol in the digest into the appropriate statistical software package (e.g., JMP Statistical Software), which then automatically predicts the GI value.

Example 2

A large number of commercially available food products and other food samples were examined using both in vivo and in vitro test protocols. Most (25 out of a total of 34) in vivo glycemic index values were determined using in vivo tests conducted by a well-known, well-respected private testing lab experienced in such testing; the remainder of such in vivo glycemic index values were taken from the scientific literature. These same samples were also examined using the in vitro method of the present invention as described in Example 1. These data were then used to calculate model parameters for the in vitro glycemic index test described herein using the MLR, PLS, and neural net methods available in JMP Statistical Software.

After the parent application was filed, it was discovered that the HCl solution used to prepare the Pepsin/Guar Gum Solution was 0.5 N rather than the desired 0.05 N. Since the Pepsin/Guar Gum Solution is used to prepare the enzyme digestion solution, the pH during enzyme digestion was about 1.1 rather than the desired about 5. This lower pH value is non-optimal for the enzyme digestion reaction. Thus, since the pH was too low, different levels of the various sugars were released relative to the fat and protein levels in the samples. However, since all samples were treated in the same manner (i.e., at the same pH during digestion), the relative values of the predicted glycemic index values remain valid. Of course, the model parameters and/or coefficients derived from this data set, would only be suitable for use if the lower pH during enzyme digestion was also used for new unknown samples. Examples 3 and 4 below were carried out using the proper HCl solution; thus the enzyme digestion reactions were carried out under more optimal pH conditions.

The following model parameters were obtained using the MLR method:

| Term | Value | Std Error | t Ratio | Prob > \|t\| |
| --- | --- | --- | --- | --- |
| Intercept | 63.080214 | 6.498483 | 9.71 | <0.0001 |
| Protein (%) | −0.974313 | 0.141985 | −6.86 | <0.0001 |
| Fat (%) | −0.67442 | 0.087795 | −7.68 | <0.0001 |
| Glucose (%) | 364.97478 | 75.57708 | 4.83 | <0.0001 |
| Fructose (%) | −452.5341 | 75.17166 | −6.02 | <0.0001 |
| Lactose (%) | −191.8138 | 84.17182 | −2.28 | 0.0311 |
| Galactose (%) | −437.3615 | 90.44204 | −4.84 | <0.0001 |
| Maltitol (%) | −298.0102 | 92.58933 | −3.22 | 0.0034 |

Thus, the equation used to estimate the in vitro glycemic index using the MLR method would be:

$$GI = 63.080214 - 0.974313\,\text{Protein}(\%) -$$
$$0.67442\,\text{Fat}(\%) + 367.97478\,\text{Glucose}(\%) -$$
$$452.5341\,\text{Fructose}(\%) - 191.8138\,\text{Lactose}(\%) -$$
$$437.3615\,\text{Galactose}(\%) - 298.0102\,\text{Maltitol}(\%).$$

The relevant statistical parameters for this model were as follows:

Summary of Fit:

| | |
| --- | --- |
| $R^2$ | 0.948355 |
| $R^2$ Adj | 0.934451 |
| Root Mean Square Error | 6.094049 |
| Mean of Response | 46.52941 |
| Observations (or Sum Wgts) | 34 |

Analysis of Variance:

| Source | DF | Sum of Squares | Mean Square | F Ratio |
| --- | --- | --- | --- | --- |
| Model | 7 | 17730.897 | 2532.99 | 68.2057 |
| Error | 26 | 965.573 | 37.14 | Prob > F |
| C. Total | 33 | 18696.471 | | <.0001 |

The following model parameters were obtained using the PLS method with five latent variables:

| Term | Value |
| --- | --- |
| Intercept | 62.745005 |
| Protein (%) | −0.986004 |
| Fat (%) | −0.670993 |
| Glucose (%) | 369.91833 |
| Fructose (%) | −446.4468 |
| Lactose (%) | −195.07 |
| Galactose (%) | −425.7489 |
| Maltitol (%) | −291.9779 |

Thus, the equation used to estimate the in vitro glycemic index using the PLS method would be:

$$GI = 62.745005 - 0.986004\,\text{Protein}(\%) - 0.670993\,\text{Fat}(\%) +$$
$$369.91833\,\text{Glucose}(\%) - 446.4468\,\text{Fructose}(\%) -$$
$$195.07\,\text{Lactose}(\%) - 425.7489\,\text{Galactose}(\%) - 291.9779\,\text{Maltitol}(\%).$$

The relevant statistical parameters for this model were as follows:

Summary of Fit:

| | |
| --- | --- |
| $R^2$ | 0.939819 |
| $R^2$ Adj | 0.937938 |
| Root Mean Square Error | 5.929726 |
| Mean of Response | 46.52941 |
| Observations (or Sum Wgts) | 34 |

The following model parameter weights were obtained using the neural net method:

| Parameter Weight | Value |
| --- | --- |
| H1: Intercept | 0.6715187765 |
| H1: Protein (%) | 0.3364859726 |
| H1: Fat (%) | 0.2031260198 |
| H1: Glucose (%) | −0.697405591 |
| H1: Fructose (%) | 0.0085016679 |
| H1: Lactose (%) | −0.162454793 |
| H1: Galactose (%) | 0.0632785954 |
| H1: Maltitol (%) | −0.053195992 |
| GI: Intercept | 3.994861093 |
| GI: H1 | −6.220038739 |

The neural net method does not provide a simple prediction equation. Rather, this method provides a series of parameter weights and a network topology which can then be used to obtain predicted results using a suitable software program (in this case the JMP Statistical Software). The fit obtained using this method is illustrated graphically in FIG. 5A. The relevant parameters for this model were as follows:

| | Specify |
| --- | --- |
| Hidden Nodes | 1 |
| Overfit Penalty | 0.01 |
| Number of Tours | 200 |
| Max Iterations | 50 |
| Converge Criterion | 0.00001 |

Results:

| SSE | 4.1349837524 |
| --- | --- |
| Penalty | 0.3981397476 |
| Total | 4.5331235 |
| N | 65 |
| 200 | Converged At Best |
| 0 | Converged Worse Than Best |
| 0 | Stuck on Flat |
| 0 | Failed to Improve |
| 0 | Reached Max Iter |

| Y | SSE | SSE Scaled | RMSE | RMSE Scaled | $R^2$ |
| --- | --- | --- | --- | --- | --- |
| GI | 1540.3848224 | 4.1349837524 | 4.94475002 | 0.25619263 | 0.9354 |

The resulting model parameters were then used to calculate the in vitro glycemic index values using each of the data fitting methods. The results from the following commercially available products were used to calculate the correlation parameters. The resulting in vitro glycemic index values determined using each of the data fitting methods are compared to the in vivo glycemic index values:

| | In vivo | In vitro GI | | |
| --- | --- | --- | --- | --- |
| Sample | GI* | PLS | MLR | Neural Net |
| Trail Mix Blend 1 | 16 | 13 | 13 | 19 |
| Trail Mix Blend 2 | 19 | 13 | 13 | 19 |
| Trail Mix Blend 3 | 20 | 21 | 21 | 21 |
| Trail Mix Blend 4 | 18 | 15 | 15 | 19 |
| Trail Mix Blend 5 | 25 | 16 | 16 | 20 |
| Trail Mix Blend 6 | 26 | 19 | 19 | 21 |
| Trail Mix Blend 7 | 35 | 37 | 37 | 30 |
| Fruit Filled Cookie 1 | 77 | 73 | 73 | 75 |
| Fruit Filled Cookie 2 | 63 | 66 | 66 | 67 |
| Peanut Brittle Bar | 38 | 34 | 34 | 28 |
| Saltine Cracker | 88 | 79 | 79 | 83 |
| Buttery Cracker | 67 | 66 | 66 | 64 |
| Chocolate Cookie | 50 | 58 | 58 | 55 |
| Baked Cracker Chip | 59 | 65 | 65 | 64 |
| Whole Wheat Cracker | 71 | 70 | 70 | 73 |
| Chocolate Chip Cookie | 45 | 52 | 52 | 45 |
| Cereal Blend | 61 | 52 | 52 | 55 |
| Cottage Cheese Mix Product | 51 | 52 | 53 | 52 |
| Potato Flakes 1 | 81 | 85 | 85 | 89 |
| Potato Flakes 2 | 89 | 83 | 84 | 88 |
| Energy Bar 1 | 31 | 36 | 36 | 34 |
| Energy Bar 2 | 36 | 42 | 42 | 39 |
| Energy Bar 3 | 27 | 38 | 38 | 35 |
| Energy Bar 4 | 40 | 39 | 40 | 37 |
| Coca-Cola | 63** | 59 | 59 | 58 |
| Whole Milk | 40** | 39 | 40 | 40 |
| Clear Unsweetened Apple Juice | 44** | 49 | 49 | 46 |
| Glucose | 100** | 99 | 99 | 96 |
| Sucrose | 68** | 64 | 64 | 65 |
| Fructose | 19** | 21 | 21 | 23 |
| Lactose | 46** | 44 | 45 | 46 |
| Maltitol | 35† | 35 | 34 | 35 |
| Galactose | 20†† | 21 | 20 | 20 |

*In vivo values were experimentally determined using a private testing laboratory unless otherwise noted.
**In vivo values taken from: "International table of glycemic index and glycemic load values," Am. J. Clin. Nutr., 76, 5-56 (2002).
†In vivo values taken from: Livesy, Nutr. Res. Rev., 16(2), 163-91 (2003).
††In vivo values taken from: Jentjens et al., Eur. J. App. I Physiol. 88, 459-465 (2003).

Figure 4:
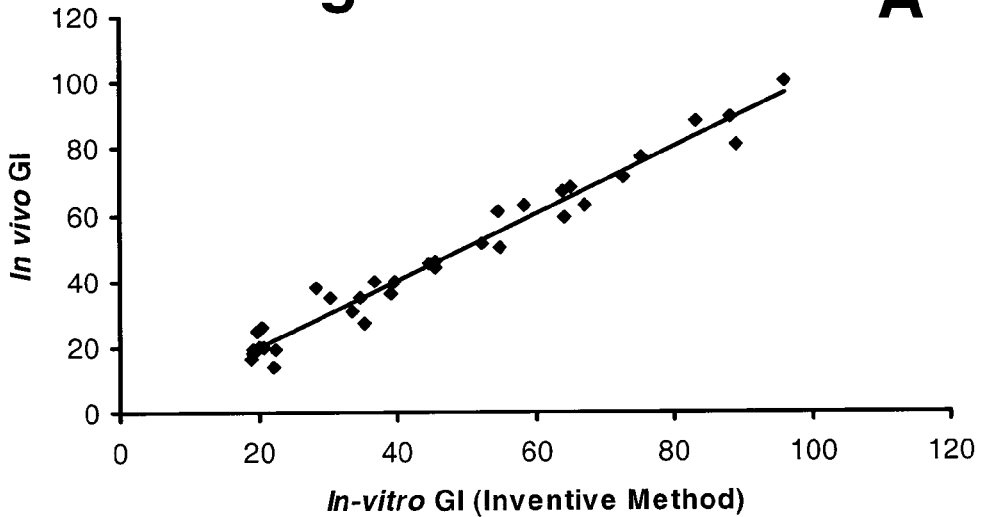
FIG. 4A provides a comparison of the known in vivo glycemic index values and the in vitro glycemic index values determined using the inventive method with neural net curve fitting procedures based on the data in Example 2; the inventive method yielded a value of 0.97 for $R^2$.
FIGS. 4B and 4C provide comparisons of the known in vivo glycemic index values and rapidly available glucose (RAG expressed as grams glucose released in 20 minutes/100 g food) as obtained using the calculation techniques used in the Englyst method (i.e., only based on the glucose release after 20 minutes digestion) with the data from Example 2.
Figure 4:
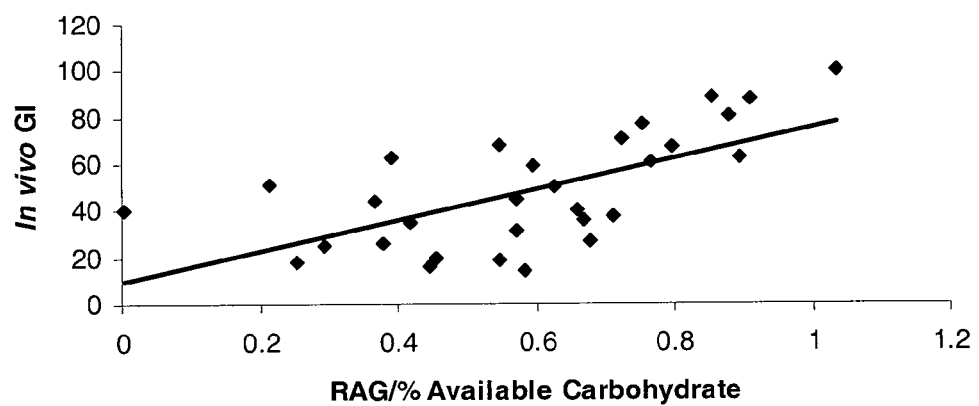
Figure 4:
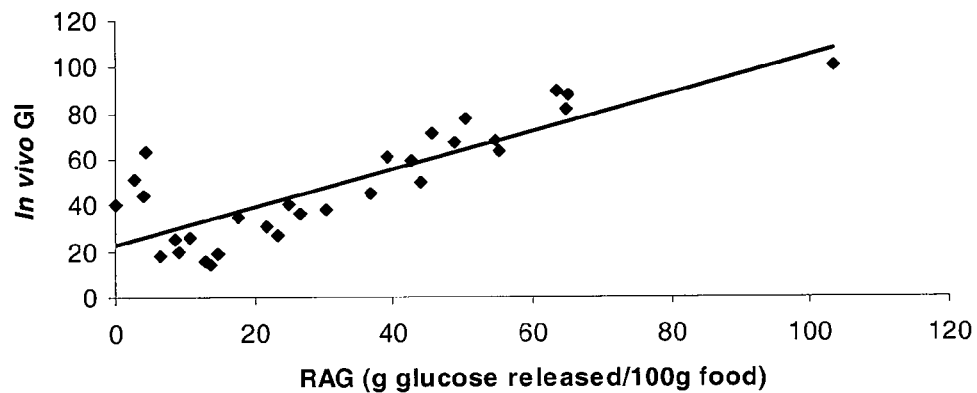

A scatter plot of this data obtained using the neural net as curve fitting procedure is shown in FIG. 4A. A $R^2$ value of 0.97 is obtained using this method. The standard deviation for the in vitro method (based on duplicate determinations of 34 total samples) was ±1.08 GI units or ±2.33 percent relative. Thus, this method appears to have very high precision and high predictive value.

Example 3

After filing the original application, work was continued and additional data points have been added and certain modifications made to the method to provide an even more accurate and precise in vitro method. As noted in Example 2 above, the pH during the enzyme digestion step in Example 2 was too low. The proper pH value for the enzyme digestion step should be about 5; other than that modification, the samples were treated in the same manner as in Example 2. Thus, 31 of the samples used in Example 2 were rerun to obtain data at the more optimal enzyme digestion pH. Additionally, 34 new samples have been added to the rerun sample from Example 2 to bring the total number of samples to 65. This in vitro method (current as of the date of this continuation-in-part application) is based on samples enzyme digested at the more optimal pH value and is presented herein. Of course, as one skilled in the art realizes, the accuracy and precision of this method is also likely to be increased even further as additional in vivo data for calibration samples and/or standards becomes available and is incorporated into the in vitro model during the calibration procedure.

The following model parameters were obtained using the MLR method:

| Term | Value | Std Error | t Ratio | Prob > \|t\| |
|---|---|---|---|---|
| Intercept | 26.779686 | 2.179648 | 12.29 | <0.0001 |
| Protein (%) | −0.967251 | 44.81633 | −8.92 | <0.0001 |
| Fat (%) | −0.385715 | 0.073903 | −5.22 | <0.0001 |
| Glucose (%) | 611.60013 | 30.00233 | 20.39 | <0.0001 |
| Lactose (%) | 301.95014 | 44.81633 | 6.74 | <0.0001 |
| Maltitol (%) | 169.03383 | 54.85795 | 3.08 | .0032 |
| (Glucose (%) − 0.05718) * (Protein (%) − 8.24967) | −18.16062 | 5.456618 | −3.33 | 0.0015 |

Thus, the equation used to estimate the in vitro glycemic index using the MLR method and the expanded data set would be:

$$GI = 26.779686 - 0.967251 \text{ Protein}(\%) -$$
$$0.385715 \text{ Fat}(\%) + 611.60013 \text{ Glucose}(\%) +$$
$$301.95014 \text{ Lactose}(\%) + 169.03383 \text{ Maltitol}(\%) -$$
$$18.16062[\text{Glucose}(\%) - 0.05718] * [\text{Protein}(\%) - 8.24967].$$

The relevant statistical parameters for this model were as follows:
Summary of Fit:

| | |
|---|---|
| $R^2$ | 0.940178 |
| $R^2$ Adj | 0.93399 |
| Root Mean Square Error | 4.958869 |
| Mean of Response | 50.4 |
| Observations (or Sum Wgts) | 65 |

Analysis of Variance:

| Source | DF | Sum of Squares | Mean Square | F Ratio |
|---|---|---|---|---|
| Model | 6 | 22415.358 | 2532.99 | 151.9250 |
| Error | 58 | 1426.242 | 24.59 | Prob > F |
| C. Total | 64 | 23841.6000 | | <.0001 |

The following model parameters were obtained using the PLS method with five latent variables:

| Term | Value |
|---|---|
| Intercept | 26.264529 |
| Protein (%) | −1.048186 |
| Fat (%) | −0.248138 |
| Glucose (%) | 621.7824 |

-continued

| Term | Value |
|---|---|
| Fructose (%) | −52.7993 |
| Lactose (%) | 233.67679 |
| Galactose (%) | −61.21071 |
| Maltitol (%) | 84.689245 |

Thus, the equation used to estimate the in vitro glycemic index using the PLS method would be:

$$GI = 26.264529 - 1.048186 \text{ Protein}(\%) -$$
$$0.248138 \text{ Fat}(\%) + 621.7824 \text{ Glucose}(\%) -$$
$$52.7993 \text{ Fructose}(\%) + 233.67679 \text{ Lactose}(\%) -$$
$$61.21071 \text{ Galactose}(\%) + 84.689245 \text{ Maltitol}(\%).$$

The relevant statistical parameters for this model were as follows:

Summary of Fit:

| | |
|---|---|
| $R^2$ | 0.930041 |
| $R^2$ Adj | 0.9289831 |
| Root Mean Square Error | 5.145383 |
| Mean of Response | 50.4 |
| Observations (or Sum Wgts) | 65 |

The following model parameter weights were obtained using the neural net method:

Neural Net Table I:

| Parameter Weight | Value |
|---|---|
| H1: Intercept | 0.6715187765 |
| H1: Protein (%) | 0.3364859726 |
| H1: Fat (%) | 0.2031260198 |
| H1: Glucose (%) | −0.697405591 |
| H1: Fructose (%) | 0.0085016679 |
| H1: Lactose (%) | −0.162454793 |
| H1: Galactose (%) | 0.0632785954 |
| H1: Maltitol (%) | −0.053195992 |
| GI: Intercept | 3.994861093 |
| GI: H1 | −6.220038739 |

As noted in Example 2, the neural net method does not provide a simple prediction equation. Rather, this method provides a series of parameter weights and a network topology which can then be used to obtain predicted results using a suitable software program (in this case the JMP Statistical Software). The fit obtained using this method is illustrated graphically in FIG. 4A. The relevant parameters for this model were as follows:

| | Specify |
|---|---|
| Hidden Nodes | 1 |
| Overfit Penalty | 0.01 |
| Number of Tours | 200 |
| Max Iterations | 50 |
| Converge Criterion | 0.00001 |

Results:

| | | | |
|---|---|---|---|
| SSE | 4.1349837524 | | |
| Penalty | 0.3981397476 | | |
| Total | 4.5331235 | | |
| N | 65 | | |
| 200 | Converged At Best | | |
| 0 | Converged Worse Than Best | | |
| 0 | Stuck on Flat | | |
| 0 | Failed to Improve | | |
| 0 | Reached Max Iter | | |

| Y | SSE | SSE Scaled | RMSE | $R^2$ |
|---|---|---|---|---|
| GI | 1540.3848224 | 4.1349837524 | 4.94475002 | 0.9354 |

The resulting model parameters were then used to calculate the in vitro glycemic index values using each of the data fitting methods as in Example 2. The results from the following products, about 33 more than in Example 2, were used to calculate correlation parameters for each model. The resulting in vitro glycemic index values determined using each of the data fitting models or methods with the expanded data set are compared to the in vivo glycemic index values:

| | | In-vitro GI | | |
|---|---|---|---|---|
| Sample | In-vivo GI* | PLS | MLR | NN |
| Trail Mix Blend 1 | 16 | 18 | 20 | 21 |
| Trail Mix Blend 2 | 19 | 17 | 20 | 20 |
| Trail Mix Blend 3 | 20 | 27 | 24 | 25 |
| Trail Mix Blend 4 | 18 | 21 | 21 | 22 |
| Trail Mix Blend 5 | 25 | 21 | 22 | 22 |
| Trail Mix Blend 6 | 26 | 22 | 23 | 23 |
| Trail Mix Blend 7 | 35 | 38 | 38 | 35 |
| Peanuts | 14** | 6 | 10 | 16 |
| Fruit Filled Cookie 1 | 77 | 69 | 71 | 70 |
| Fruit Filled Cookie 2 | 63 | 64 | 67 | 65 |
| Peanut Brittle Bar | 38 | 32 | 31 | 29 |
| Saltine Cracker*** | 74** | 69 | 67 | 69 |
| Buttery Cracker | 67 | 69 | 67 | 67 |
| Chocolate Cookie | 50 | 50 | 50 | 47 |
| Baked Cracker Chip | 59 | 68 | 68 | 67 |
| Whole Wheat Cracker | 71 | 68 | 66 | 67 |
| Chocolate Chip Cookie | 45 | 49 | 47 | 44 |
| Breakfast Cereal 1 | 63‡‡ | 58 | 59 | 57 |
| Breakfast Cereal 2 | 47‡‡ | 50 | 49 | 49 |
| Breakfast Cereal 3 | 61** | 61 | 63 | 61 |
| Breakfast Cereal 4 | 81** | 76 | 78 | 78 |
| Breakfast Cereal 5 | 74** | 68 | 68 | 69 |
| Multi-Grain Instant Oatmeal | 55‡‡ | 67 | 64 | 67 |
| Ice Cream, full fat, vanilla | 61** | 61 | 63 | 61 |
| Cottage Cheese Mix Product | 51 | 42 | 45 | 41 |
| Potato Flakes‡‡‡ | 85 | 76 | 76 | 78 |
| Baked Potato | 60** | 61 | 61 | 60 |
| Energy Bar 1 | 31 | 29 | 32 | 29 |
| Energy Bar 2 | 36 | 36 | 35 | 34 |
| Energy Bar 3 | 27 | 35 | 33 | 33 |
| Energy bar 4 | 40 | 35 | 34 | 33 |
| Coca-Cola**** | 58** | 51 | 53 | 51 |
| Whole Milk | 40** | 39 | 40 | 39 |
| Apple Juice | 44** | 44 | 44 | 44 |
| Orange Juice 1 | 50** | 53 | 54 | 53 |
| Orange Juice 2 | 50** | 51 | 53 | 51 |
| Cranberry Juice Cocktail | 60** | 57 | 60 | 58 |
| Whole Wheat Hamburger Bun | 62‡‡ | 73 | 70 | 74 |
| Hot Dog Bun | 71** | 71 | 71 | 72 |
| White Bread | 71** | 70 | 71 | 71 |
| Whole Wheat Bread | 62** | 61 | 61 | 60 |
| Pretzels | 83** | 77 | 75 | 79 |
| Popcorn (Microwave, Butter Flavor) | 72 | 75 | 71 | 73 |
| Raisin Bran Flax Muffin | 52‡‡ | 53 | 55 | 52 |
| Rice, Brown, Long Grain | 55** | 62 | 62 | 61 |
| Rice, White, Long Grain | 69** | 68 | 70 | 69 |
| Rice and Corn Snack | 81‡‡ | 80 | 81 | 82 |
| Whole Wheat Pasta | 57‡‡ | 63 | 60 | 62 |
| Grapes | 46** | 49 | 49 | 48 |
| Orange | 48** | 45 | 45 | 44 |
| Peaches, Canned | 38** | 45 | 45 | 45 |
| Banana | 47** | 44 | 43 | 43 |
| Apple | 38** | 42 | 41 | 42 |
| Pear | 38** | 33 | 30 | 33 |
| Corn (Canned Yellow Sweet Kernels) | 46** | 46 | 45 | 44 |
| Carrots (Fresh Baby) | 47** | 43 | 41 | 41 |
| Vegetarian Chili | 36‡‡ | 38 | 40 | 36 |
| Tomato and Basil Pasta Sauce | 33‡‡ | 43 | 42 | 42 |
| Pasta Fagiola Soup | 52‡‡ | 64 | 66 | 64 |
| Glucose | 100** | 92 | 99 | 95 |
| Sucrose | 61‡ | 57 | 60 | 58 |
| Fructose | 19** | 21 | 18 | 26 |
| Lactose | 46** | 49 | 47 | 49 |
| Maltitol | 35† | 35 | 35 | 35 |
| Galactose | 20†† | 20 | 18 | 20 |

*In vivo values were experimentally determined using a private testing laboratory unless otherwise noted.
**In vivo values taken from: "International table of glycemic index and glycemic load values," Am. J. Clin. Nutr., 76, 5-56 (2002).
***This in vivo value for Saltine Cracker differs from that used in Example 2. This present value appears to be more accurate.
****This in vivo value, based on an average for two determinations, for Coca-Cola differs from that used in Example 2 which was based on only one determination. This present value appears to be more accurate.
‡In vivo value taken from: "International table of glycemic index and glycemic load values," Am. J. Clin. Nutr., 76, 5-56 (2002) (outliers excluded). Thus, this value differs slightly from the one used in Example 2.
‡‡In vivo values taken from manufacturer's data.
‡‡‡This in vivo value for Potato Flakes is an average of Potato Flakes 1 and Potato Flakes 2 in Example 2. The two Potato Flake samples in Example 2 were determined to be very similar in nature.
†In vivo values taken from: Livesy, Nutr. Res. Rev., 16(2), 163-91 (2003).
††In vivo values taken from: Jentjens et al., Eur. J. App. Physiol. 88, 459-465 (2003).

Figure 5:
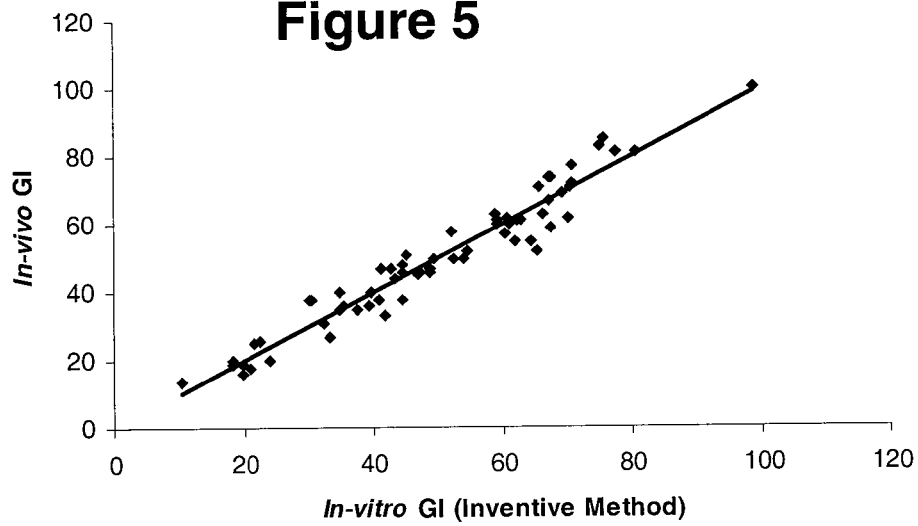
FIG. 5A provides a comparison of the known in vivo glycemic index values and the in vitro glycemic index values determined using the inventive method with multiple linear regression curve fitting procedures based on the data in Example 3; the inventive method yielded a value of 0.94 for $R^2$.
FIGS. 5B and 5C provide comparisons of the known in vivo glycemic index values and rapidly available glucose (RAG expressed as grams glucose released in 20 minutes/100 g food) as obtained using the calculation techniques used in the Englyst method (i.e., only based on the glucose release after 20 minutes digestion) with the data from Example 3.
Figure 5:
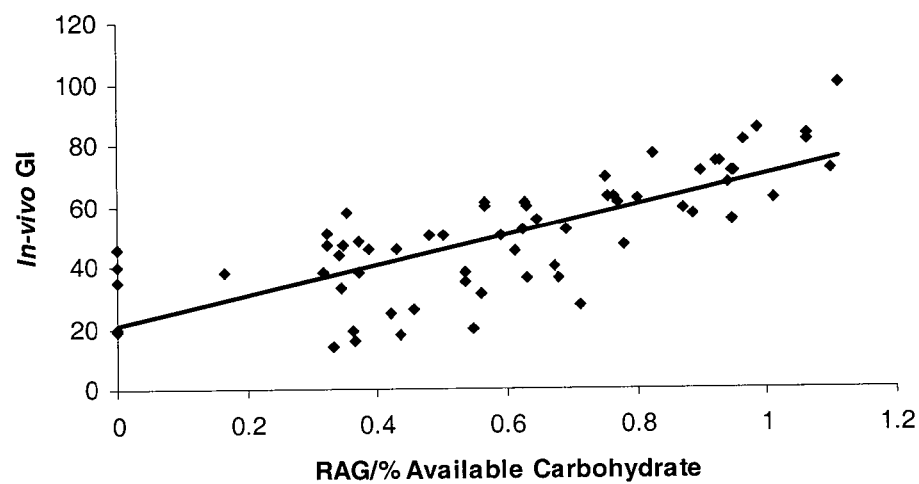
Figure 5:
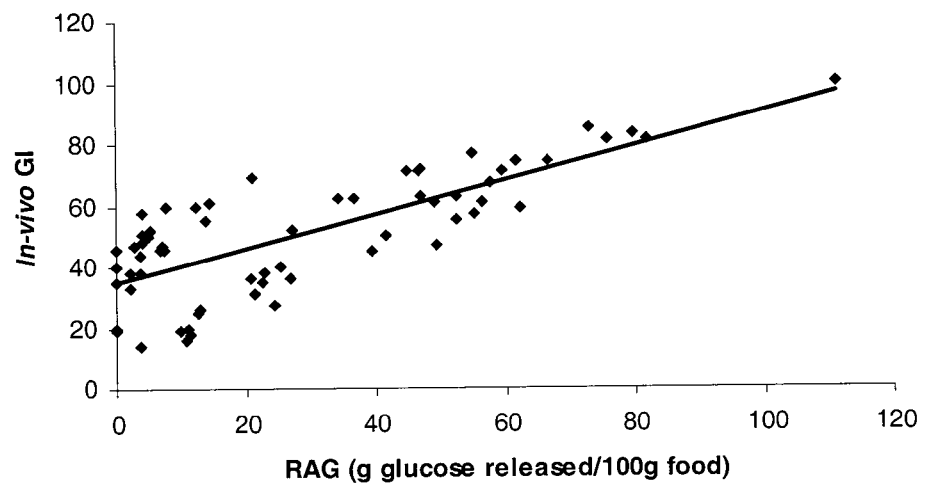

A scatter plot of this data obtained using the MLR curve fitting procedure is shown in FIG. 5A. A $R^2$ value of 0.94 is obtained using this method. The standard deviation for the in vitro method (based on duplicate determinations of 65 total samples) was ±4 GI units or +6 percent relative. Thus, this method appears to have very high precision and high predictive value.

The in vitro method can then be used to calculate the in vitro GI value for an unknown food product or food ingredient by simply carrying out the method described herein for the sample preparation and analysis and using the data and the desired predictive equation determined from the calibration data. Of course, as demonstrated by comparing Examples 2 and 3, the calibration results and predictive equation data will depend on the actual conditions under which the calibration data set and unknown samples are analyzed (especially as regard to the enzyme digestion step). However, as long as the same procedure is used for all samples, variations in the analysis procedure do not appear to significantly effect the predictive ability of the present method even when the predictive equations differ widely. This, we believe, demonstrates the robustness of this in vitro method. As the size of the calibration data set is increased, either in number of samples and/or accuracy of the in vivo GI values used, the accuracy and precision of the method is expected to increase.

As noted above, Garsetti et al. provided a scatter plot with an $R^2$ value of 0.25 for the in vitro Englyst method, thus indicating that this method had little predictive value. For further comparison purposes, the rapidly available glucose (RAG as expressed as grams glucose released in 20 minutes/100 g food) as obtained using the calculation techniques used in the Englyst method (i.e., only based on the glucose release after 20 minutes digestion) on the data from Examples 2 and 3 were separately correlated to in vivo GI values using the calculations and parameters described in the in vitro Englyst method (i.e., using only glucose released after 20 minutes) as detailed in Englyst et al., Brit. J. Nutr., 75, 327-337 (1996) (FIG. 4B) and Englyst et al., Am. J. Clin. Nutr., 69, 448-454 (1999) (FIG. 4C). Such scatter plots are shown in FIGS. 4B and 4C using the Example 2 data and in FIGS. 5B and 5C using the Example 4 data. In FIGS. 4B and 5B, the in vivo GI is plotted versus RAG/(% Available Carbohydrates) for the Example 2 and Example 3 data, respectively; in FIGS. 4C and 5C, the in vivo GI is plotted versus RAG for the Example 2 and Example 3 data, respectively. When such calculations were carried out using Example 2 data, the $R^2$ values of the Englyst et al. method increased to about 0.41 and about 0.68 in FIGS. 4B and 4C, respectively; using the Example 3 data, the $R^2$ values of the Englyst et al. method increased to about 0.56 and about 0.58 in FIGS. 5B and 5C, respectively. Although these represent improvements as compared to the Garsetti et al. scatter plot, the predictive value of the method is still poor.

We believe, as demonstrated by the $R^2$ value of about 0.94 to about 0.97 (depending on the specific curve fitting method used and the conditions under which the data is generated) for the present inventive method, that, for the first time, an in vitro method has been provided which can be used to accurately and precisely determine glycemic index values for a wide variety of food products and/or food ingredients. This method can be used to easily, quickly, and inexpensively obtain accurate glycemic index values which compare favorably in terms of accuracy to the much more time consuming and expensive human subject in vivo testing currently recommended. Moreover, the accuracy and precision of this method is likely to be increased even further as additional in vivo data for calibration samples and/or standards becomes available and is incorporated into the in vitro model during the calibration procedure. This advance in the art should increase the usefulness of glycemic index and related values (e.g., glycemic load values determined by multiplying the glycemic index by the amount of carbohydrate in grams provided by a food and dividing the total by 100) in human nutrition.

Example 4

The samples used in Example 2 (using a less than optimal pH value in the enzymatic reaction step) were rerun in Example 3 using a more optimal pH value. The data from Example 3 for only the rerun Example 2 data set (i.e., excluding the additional samples added in Example 3) was used to generate a new set of the various curve fitting parameters. This example—which is based on 31 of the 34 samples of Example 2—effectively illustrates the in vitro analysis of Example 2 with the samples run at a more optimal pH value. This allows for a more direct comparison of the correlation coefficients or parameters from Example 2 and Example 3 where only the number of samples in each data set was varied.

The following model parameters for this modified data set were obtained using the MLR method:

| Term | Value | Std Error | t Ratio | Prob > \|t\| |
|---|---|---|---|---|
| Intercept | 30.502796 | 3.388751 | 9.00 | <0.0001 |
| Protein (%) | −0.787639 | 0.137003 | −5.75 | <0.0001 |
| Fat (%) | −0.515649 | 0.088565 | −5.82 | <0.0001 |
| Glucose (%) | 573.03525 | 51.23366 | 11.18 | <0.0001 |
| Lactose (%) | 275.61246 | 45.69519 | 6.03 | <0.0001 |
| Maltitol (%) | 147.62386 | 51.90435 | 2.84 | 0.0090 |

-continued

| Term | Value | Std Error | t Ratio | Prob > \|t\| |
|---|---|---|---|---|
| (Glucose (%) − 0.05091) * (% Protein − 10.0429) | −20.39966 | 6.583621 | −3.10 | 0.0049 |

Thus, the equation used to estimate the in vitro glycemic index using the MLR method:

$$GI = 30.502796 - 0.787639 \text{ Protein}(\%) -$$
$$0.515649 \text{ Fat}(\%) + 573.03525 \text{ Glucose}(\%) +$$
$$275.61246 \text{ Lactose}(\%) + 147.62386 \text{ Maltitol}(\%) -$$
$$20.39966[\text{Glucose}(\%) - 0.05091] * [\text{Protein}(\%) - 10.0429].$$

The relevant statistical parameters for this model were as follows:

Summary of Fit:

| | |
|---|---|
| $R^2$ | 0.968035 |
| $R^2$ Adj | 0.960043 |
| Root Mean Square Error | 4.393218 |
| Mean of Response | 45.03226 |
| Observations (or Sum Wgts) | 31 |

Analysis of Variance:

| Source | DF | Sum of Squares | Mean Square | F Ratio |
|---|---|---|---|---|
| Model | 6 | 14027.759 | 2337.96 | 121.1355 |
| Error | 24 | 463.209 | 19.31 | Prob > F |
| C. Total | 30 | 14490.968 | | <.0001 |

The following model parameters were obtained using the PLS method with five latent variables:

| Term | Value |
|---|---|
| Intercept | 48.443999 |
| Protein (%) | −1.003763 |
| Fat (%) | −0.492915 |
| Glucose (%) | 443.60721 |
| Fructose (%) | −265.4383 |
| Lactose (%) | −33.78516 |
| Galactose (%) | −277.1671 |
| Maltitol (%) | −142.2773 |

Thus, the equation used to estimate the in vitro glycemic index using the PLS method would be:

$$GI = 48.443999 - 1.003763 \text{ Protein}(\%) -$$
$$0.492915 \text{ Fat}(\%) + 443.60721 \text{ Glucose}(\%) -$$
$$265.4383 \text{ Fructose}(\%) - 33.78516 \text{ Lactose}(\%) -$$
$$277.1671 \text{ Galactose}(\%) - 142.2773 \text{ Maltitol}(\%).$$

The relevant statistical parameters for this model were as follows:

Summary of Fit:

| | |
|---|---|
| $R^2$ | 0.964188 |
| $R^2$ Adj | 0.962953 |
| Root Mean Square Error | 4.230216 |
| Mean of Response | 45.03226 |
| Observations (or Sum Wgts) | 31 |

The following model parameter weights were obtained using the neural net method:

Neural Net Table I:

| Parameter Weight | Value |
|---|---|
| H1: Intercept | 0.8572040599 |
| H1: Protein (%) | 0.3767226601 |
| H1: Fat (%) | 0.4495966298 |
| H1: Glucose (%) | −0.651892945 |
| H1: Fructose (%) | 0.2134796555 |
| H1: Lactose (%) | −0.042105783 |
| H1: Galactose (%) | 0.2610403756 |
| H1: Maltitol (%) | 0.0659243194 |
| GI: Intercept | 3.2202762866 |
| GI: H1 | −4.803405337 |

As noted in Examples 2 and 3, the neural net method does not provide a simple prediction equation. Rather, this method provides a series of parameter weights and a network topology which can then be used to obtain predicted results using a suitable software program (in this case the JMP Statistical Software). The relevant parameters for this model were as follows:

| | Specify |
|---|---|
| Hidden Nodes | 1 |
| Overfit Penalty | 0.01 |
| Number of Tours | 200 |
| Max Iterations | 50 |
| Converge Criterion | 0.00001 |

Results:

| | | | |
|---|---|---|---|
| SSE | | | 1.027472638 |
| Penalty | | | 0.2469635769 |
| Total | | | 1.2744362149 |
| N | | | 31 |
| 200 | | | Converged At Best |
| 0 | | | Converged Worse Than Best |
| 0 | | | Stuck on Flat |
| 0 | | | Failed to Improve |
| 0 | | | Reached Max Iter |

| Y | SSE | SSE Scaled | RMSE | $R^2$ |
|---|---|---|---|---|
| GI | 496.30242843 | 1.027472638 | 4.13689217 | 0.9658 |

The resulting model parameters were then used to calculate the in vitro glycemic index values using each of the data fitting methods. The results from the following commercially available products were used to calculate the correlation parameters. The resulting in vitro glycemic index values determined using each of the data fitting methods are compared to the in vivo glycemic index values:

| | | In vitro GI | | |
|---|---|---|---|---|
| Sample* | In vivo GI** | PLS | MLR | Neural Net |
| Trail Mix Blend 1 | 16 | 19 | 19 | 21 |
| Trail Mix Blend 2 | 19 | 18 | 19 | 21 |
| Trail Mix Blend 3 | 20 | 19 | 22 | 21 |
| Trail Mix Blend 4 | 18 | 19 | 20 | 21 |
| Trail Mix Blend 5 | 25 | 20 | 21 | 22 |
| Trail Mix Blend 6 | 26 | 20 | 21 | 22 |
| Trail Mix Blend 7 | 35 | 37 | 38 | 33 |
| Peanuts | 14** | 6 | 10 | 16 |
| Fruit Filled Cookie 1 | 77 | 71 | 73 | 72 |
| Fruit Filled Cookie 2 | 63 | 65 | 69 | 66 |
| Peanut Brittle Bar | 38 | 33 | 30 | 29 |
| Saltine Cracker | 74 | 73 | 69 | 74 |
| Buttery Cracker | 67 | 68 | 67 | 66 |
| Chocolate Cookie | 50 | 50 | 47 | 45 |
| Baked Cracker Chip | 59 | 70 | 69 | 70 |
| Whole Wheat Cracker | 71 | 72 | 67 | 73 |
| Chocolate Chip Cookie | 45 | 50 | 47 | 45 |
| Cottage Cheese Mix Product | 51 | 48 | 47 | 47 |
| Potato Flakes | 85 | 81 | 79 | 84 |
| Energy Bar 1 | 31 | 31 | 35 | 31 |
| Energy Bar 2 | 36 | 37 | 37 | 36 |
| Energy Bar 3 | 27 | 35 | 35 | 34 |
| Energy Bar 4 | 40 | 35 | 36 | 35 |
| Coca-Cola | 58 | 53 | 55 | 53 |
| Whole Milk | 40 | 41 | 40 | 41 |
| Clear Unsweetened Apple Juice | 44 | 50 | 46 | 48 |
| Glucose | 100 | 95 | 102 | 96 |
| Sucrose | 61 | 58 | 62 | 59 |
| Fructose | 19 | 21 | 20 | 25 |
| Lactose | 46 | 45 | 47 | 47 |
| Maltitol | 35 | 34 | 35 | 35 |
| Galactose | 20 | 20 | 20 | 20 |

*Since the cereals used in Examples 2 and 3 were different, they were omitted from this data set.
**In vivo values were taken from Example 3 where they were derived as explained therein.

Figure 6:
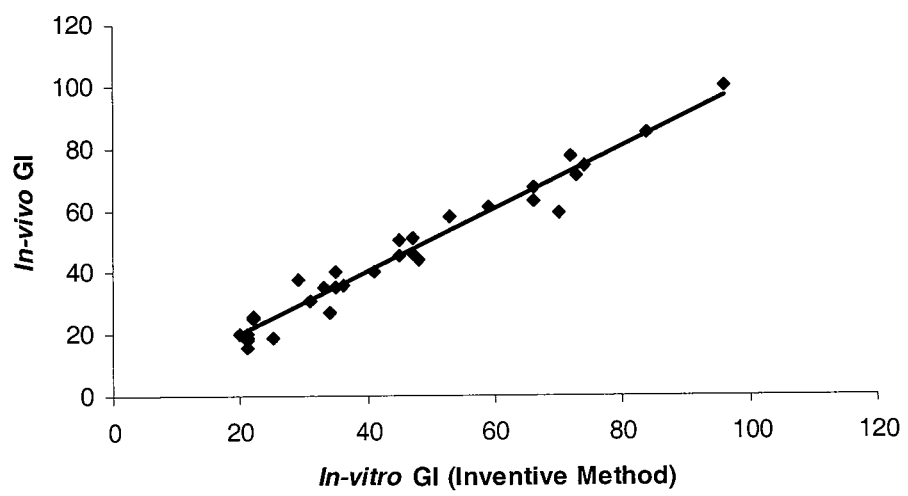
FIG. 6 provides a comparison of the known in vivo glycemic index values and the in vitro glycemic index values determined using the inventive method with neural net curve fitting procedures based on the data in Example 4; the inventive method yielded a value of 0.96 for $R^2$.

A scatter plot of this data obtained using the neural net curve fitting procedure is shown in FIG. 6. A $R^2$ value of 0.96 is obtained using this method. Thus, again this method appears to have very high precision and high predictive value. The results of Examples 3 and 4, based on different number of samples but all run under similar conditions, generally agree.

As demonstrated in these Examples (especially in Examples 3 and 4), as the number of samples increases, the values of the various coefficients and other parameters used in the various curve fitting procedures are expected to be refined to achieve the best fit for the data set. Additional samples added to the data set are expected to increase the diversity of food products and better represent larger populations of food products.

What is claimed is:

1. An in vitro method for determining a predicted glycemic index for a test food product, said method comprising
    (1) determining protein content and fat content of a portion of the test food product;
    (2) providing another portion of the test food product in an essentially homogeneous and finely divided state to provide a test food sample;
    (3) digesting a sufficient amount of the test food sample in the essentially homogeneous and finely divided state in a two-step in vitro digestion to provide a standardized amount of available carbohydrate with a mixture of digestive enzymes for a fixed period of time to provide a digested sample, wherein the two-step in vitro digestion involves a first digestion using an enzyme to hydrolyze proteins and a second step utilizing a mixture of enzymes for digestion of carbohydrates to produce sugars;

(4) treating the digested sample in its entirety immediately upon the fixed period of time to stop enzymatic reactions, wherein the digested sample remains as a single, whole sample until at least when the digested sample is treated;

(5) determining amounts of glucose and at least two sugars or sugar alcohols selected from the group consisting of fructose, galactose, lactose, sucrose, and maltitol in the digestive sample from step (4);

(6) performing steps (1) through (5) on calibration samples to determine (i) protein content, (ii) fat content, (iii) amount of glucose, and (iv) amount of at least two additional sugars for the calibration samples;

(7) determining in vivo glycemic index values for the calibration samples, the in vivo glycemic index values having been determined from blood samples;

(8) comparing the protein content, the fat content, the amount of glucose, and the amount of at least two additional sugars for the calibration samples from step (6) to the in vivo glycemic index values for the calibration samples from step (7) to generate a predictive equation; and (9) determining in a processing device, the predicted glycemic index of the test food product using the predictive equation from step (8).

2. The in vitro method of claim 1, wherein the amounts of all listed sugars and sugar alcohols in step (5) are determined and used to calculated the glycemic index in step (9).

3. The in vitro method of claim 1, wherein the test food product is obtained in the essentially homogeneous and finely divided state by grinding the test food product at a temperature below about −40° C.

4. The in vitro method of claim 2, wherein the test food product is obtained in the essentially homogeneous and finely divided state by grinding the test food product at a temperature of about −78° C. or less.

5. The in vitro method of claim 1, wherein test food product is obtained in the essentially homogeneous and finely divided state by grinding the test food product at a temperature at or near liquid nitrogen temperatures.

6. The in vitro method of claim 2, wherein test food product is obtained in the essentially homogeneous and finely divided state by grinding the test food product at a temperature at or near liquid nitrogen temperatures.

7. The in vitro method of claim 1, wherein the amounts of glucose and the at least two sugars or sugar alcohols selected from the group consisting of fructose, galactose, lactose, sucrose, and maltitol in the digestive sample from step (4) are determined using high performance ion chromatography.

8. The in vitro method of claim 2, wherein the amounts of glucose and the sugars or sugar alcohols in the digestive sample from step (4) are determined using high performance ion chromatography.

9. The in vitro method of claim 1, wherein the test food product is obtained in the essentially homogeneous and finely divided state by grinding the test food product at a temperature below about −40° C. and wherein the amounts of glucose and the at least two sugars or sugar alcohols selected from the group consisting of fructose, galactose, lactose, sucrose, and maltitol in the digestive sample from step (4) are determined using high performance ion chromatography.

10. The in vitro method of claim 2, wherein the test food product is obtained in the essentially homogeneous and finely divided state by grinding the test food product at a temperature below about −40° C. and wherein the amounts of glucose, fructose, galactose, lactose, sucrose, and maltitol in the digestive sample from step (4) are determined using high performance ion chromatography.

11. An in vitro method for determining a predicted glycemic index for a test food product, said method comprising (1) determining protein content and fat content of a portion of the test food product;

(2) grinding another portion of the test food product at or near liquid nitrogen temperatures to provide a test food sample in an essentially homogeneous and finely divided state;

(3) digesting a sufficient amount of the test food sample in the essentially homogeneous and finely divided state in a two-step in vitro digestion to provide a standardized amount of available carbohydrate with a mixture of digestive enzymes for a fixed period of time to provide a digested sample, wherein the two-step in vitro digestion involves a first digestion using an enzyme to hydrolyze proteins and a second step utilizing a mixture of enzymes for digestion of carbohydrates to produce sugars;

(4) treating the digested sample in its entirety immediately upon the fixed period of time to stop enzymatic reactions;

(5) calculating amounts of glucose, fructose, galactose, lactose, sucrose, and maltitol in the digestive sample from step (4) using high performance ion chromatography;

(6) performing steps (1) through (5) on calibration samples to determine (i) protein content, (ii) fat content, (iii) amount of glucose, (iv) amount of fructose, (v) amount of galactose, (vi) amount of lactose, (vii) amount of sucrose, and (viii) amount of maltitol for the calibration samples;

(7) determining in vivo glycemic index values for the calibration samples, the in vivo glycemic index values having been determined from blood samples;

(8) comparing the protein content, the fat content, the amount of glucose, the amount of fructose, the amount of galactose, the amount of lactose, the amount of sucrose, and the amount of maltitol for the calibration samples from step (6) to the in vivo glycemic index values for the calibration samples from step (7) to generate a predictive equation or predictive method; and (9) determining the predicted glycemic index of the test food product using the predictive equation or predictive method from step (8).

12. The in vitro method of claim 11, wherein the predictive equation or predictive method is derived from multivariate analysis using a curve fitting procedure selected from the group consisting of multiple linear regression, partial least squares, and neural net.

13. The in vitro method of claim 11, wherein the curve fitting procedure is multiple linear regression.

14. The in vitro method of claim 11, wherein the curve fitting procedure is partial least squares.

15. The in vitro method of claim 11, wherein the curve fitting procedure is neural net.

16. An in vitro method for determining a predicted glycemic index for a test food product, said method comprising (1) determining protein content and fat content of a portion of the test food product;

(2) providing another portion of the test food product in an essentially homogeneous and finely divided state to provide a test food sample;

(3) digesting a sufficient amount of the test food sample in the essentially homogeneous and finely divided state in a two-step in vitro digestion to provide a standardized amount of available carbohydrate with a mixture of digestive enzymes for a fixed period of time to provide a digested sample, wherein the two-step in vitro digestion involves a first digestion using an enzyme to hydrolyze proteins and a second step utilizing a mixture of enzymes for digestion of carbohydrates to produce sugars;

(4) treating the digested sample in its entirety immediately upon the fixed period of time to stop enzymatic reactions;

(5) determining amounts of glucose and at least two sugars or sugar alcohols selected from the group consisting of fructose, galactose, lactose, sucrose, and maltitol in the digestive sample from step (4);

(6) determining protein content and fat content for calibration samples;

(7) determining amounts of glucose and at least two sugars or sugar alcohols selected from the group consisting of fructose, galactose, lactose, sucrose, and maltitol for the calibration samples using steps (2) through (4);

(8) determining in vivo glycemic index values for the calibration samples, the in vivo glycemic index values having been determined from blood samples;

(9) comparing the protein content, the fat content, the amount of glucose and the amount of at least two sugars selected from the group consisting of fructose, galactose, lactose, sucrose, and maltitol in the calibration samples from steps (6) and (7) to the in vivo glycemic index values for the calibration samples from step (8) to generate a predictive equation or predictive method; and

(10) determining in a processing device, the predicted glycemic index of the test food product using the predictive equation or predictive method from step (9).

17. The in vitro method of claim 1, wherein pepsin is added to begin hydrolysis of proteins and at least one of the group consisting of pancreatin, amyloglucosidase, and invertase is added to digest carbohydrates.

18. The in vitro method of claim 1, wherein the fixed period of time is about 20 minutes.

19. The in vitro method of claim 1, wherein the standardized amount of available carbohydrates is about 0.2 to about 1 g.

20. The in vitro method of claim 16, wherein the predictive equation is selected from the group consisting of Equations 1-6, wherein Equation 1 is Predicted GI=63.080214−0.974313×(protein concentration)−0.67442×(fat concentration)+367.97478×(glucose concentration)−452.5341×(fructose concentration)−191.8138×(lactose concentration)−437.3615×(galactose concentration)−298.0102×(maltitol concentration);

Equation 2 is Predicted GI=62.745005−0.986004×(protein concentration)−0.670993×(fat concentration)+369.91833×(glucose concentration)−446.4468×(fructose concentration)−195.07×(lactose concentration)−425.7489×(galactose concentration)−291.9779×(maltitol concentration);

Equation 3 is Predicted GI=26.779686−0.967251×(protein concentration)−0.385715×(fat concentration)+611.60013×(glucose concentration)+301.95014×(lactose concentration)+169.03383×(maltitol concentration)−18.16062×[(glucose concentration)−0.05718]×[(protein concentration)−8.24967];

Equation 4 is Predicted GI=26.264529−1.048186×(protein concentration)−0.248138×(fat concentration)+621.7824×(glucose concentration)−52.7993×(fructose concentration)+233.67679×(lactose concentration)−61.21071×(galactose concentration)+84.689245×(maltitol concentration);

Equation 5 is Predicted GI=30.502796−0.787639×(protein concentration)−0.515649×(fat concentration)+573.03525×(glucose concentration)+275.61246×(lactose concentration)+147.62386×(maltitol concentration)−20.39966×[(glucose concentration)−0.05091]×[(protein concentration)−10.0429]; and Equation 6 is Predicted GI=48.443999−1.003763×(protein concentration)−0.492915×(fat concentration)+443.60721×(glucose concentration)−265.4383×(fructose concentration)−33.78516×(lactose concentration)−277.1671×(galactose concentration)−142.2773×(maltitol concentration).

21. An in vitro method for determining a predicted glycemic index for a test food product, said method comprising:
(A) determining a predictive equation based on calibration samples;
(1) determining protein content and fat content of a portion of each calibration sample;
(2) providing another portion of each calibration sample in an essentially homogeneous and finely divided state to provide a respective calibration food sample;
(3) digesting a sufficient amount of each calibration food sample in the essentially homogeneous and finely divided state in a two-step in vitro digestion to provide a standardized amount of available carbohydrate with a mixture of digestive enzymes for a fixed period of time to provide a digested calibration sample, wherein the two-step in vitro digestion involves a first digestion using an enzyme to hydrolyze proteins and a second step utilizing a mixture of enzymes for digestion of carbohydrates to produce sugars;
(4) treating the digested calibration sample in its entirety immediately upon the fixed period of time to stop enzymatic reactions, wherein the digested calibration sample remains as a single, whole sample until at least when the digested calibration sample is treated;
(5) determining amounts of glucose and at least two sugars or sugar alcohols selected from the group consisting of fructose, galactose, lactose, sucrose, and maltitol in the digested calibration sample from step (4);
(6) determining in vivo glycemic index values for the calibration samples, the in vivo glycemic index values having been determined from blood samples;
(7) comparing the protein content, the fat content, the amount of glucose, and the amount of at least two additional sugars for the calibration samples from steps (1) and (5) to the in vivo glycemic index values for the calibration samples from step (6) to generate a predictive equation;
(B) analyzing the test food product;
(1) determining protein content and fat content of a portion of the test food product;
(2) providing another portion of the test food product in an essentially homogeneous and finely divided state to provide a test food sample;
(3) digesting a sufficient amount of the test food sample in the essentially homogeneous and finely divided state in a two-step in vitro digestion to provide a standardized amount of available carbohydrate with a mixture of digestive enzymes for a fixed period of time to provide a digested sample, wherein the two-step in vitro digestion involves a first digestion using an enzyme to hydrolyze proteins and a second step utilizing a mixture of enzymes for digestion of carbohydrates to produce sugars;
(4) treating the digested sample in its entirety immediately upon the fixed period of time to stop enzymatic reactions, wherein the digested sample remains as a single, whole sample until at least when the digested sample is treated;
(5) determining amounts of glucose and at least two sugars or sugar alcohols selected from the group consisting of fructose, galactose, lactose, sucrose, and maltitol in the digestive sample from step (4);
(6) determining in a processing device, the predicted glycemic index of the test food product using the protein content, the fat content, the amount of glucose and the amount of at least two sugars of the test food product from step (5) in the predictive equation from step (A).

* * * * *